US009696312B2

(12) United States Patent
Suciu-Foca et al.

(10) Patent No.: US 9,696,312 B2
(45) Date of Patent: Jul. 4, 2017

(54) DIAGNOSIS AND TREATMENT OF CANCER EXPRESSING ILT3 OR ILT3 LIGAND

(75) Inventors: Nicole Suciu-Foca, New York, NY (US); George Vlad, Forest Hills, NY (US); Chih-Chao Chang, Scarsdale, NY (US); Zhuoru Liu, New York, NY (US); Adriana Ioana Colovai, Dumont, NJ (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 14/342,440

(22) PCT Filed: Sep. 4, 2012

(86) PCT No.: PCT/US2012/053714
§ 371 (c)(1),
(2), (4) Date: Nov. 7, 2014

(87) PCT Pub. No.: WO2013/033734
PCT Pub. Date: Mar. 7, 2013

(65) Prior Publication Data
US 2015/0110714 A1 Apr. 23, 2015

Related U.S. Application Data

(60) Provisional application No. 61/530,936, filed on Sep. 2, 2011, provisional application No. 61/590,510, filed on Jan. 25, 2012.

(51) Int. Cl.
| A61K 47/48 | (2006.01) |
| G01N 33/574 | (2006.01) |
| C07K 16/28 | (2006.01) |
| C07K 14/705 | (2006.01) |

(52) U.S. Cl.
CPC ... *G01N 33/57492* (2013.01); *A61K 47/4863* (2013.01); *A61K 47/48376* (2013.01); *C07K 14/705* (2013.01); *C07K 16/28* (2013.01); *C07K 16/2803* (2013.01); *G01N 33/57426* (2013.01); *G01N 33/57484* (2013.01); *G01N 2333/70596* (2013.01); *G01N 2458/00* (2013.01)

(58) Field of Classification Search
CPC .................. G01N 33/57426–33/47492; A61K 47/48723–47/48761; A61K 47/48376–47/4863; C07K 16/28; C07K 16/2803; C07K 16/30–16/3092
See application file for complete search history.

(56) References Cited

U.S. PATENT DOCUMENTS

| 2007/0041982 A1* | 2/2007 | Ponath | C07K 14/70503 424/155.1 |
| 2008/0311073 A1* | 12/2008 | Suciu-Foca | C07K 14/70503 424/85.2 |
| 2009/0202544 A1* | 8/2009 | Suciu-Foca | A61K 35/14 424/138.1 |
| 2009/0274685 A1 | 11/2009 | Suciu-Foca et al. | |

FOREIGN PATENT DOCUMENTS

| WO | 2010/056337 A2 | 5/2010 |
| WO | 2013/036282 A2 | 3/2013 |
| WO | WO2017/015227 A1 * | 1/2017 |

OTHER PUBLICATIONS

Colovai et al., Cytometry Part B (Clinical Cytometry) Jan. 31, 2007; 72B:354-363.*
Cella et al., J. Exp. Med. 1997; 185:1743-51.*
Kim-Schulze et al., J. Immunol. 2006; 176:2790-98.*
Bartolazzi et al., The Lancet 2008; 9:543-49.*
Anderson & Allen, Immunol. 2009; 127:8-17.*
Cheng et al., J. Biol. Chem., 2011; 286:18013-025.*
HogenEsch et al. J. Controlled Release 2012; 164:183-186.*
Tang et al. Cancer Letters 2016; 370:85-90.*
Vitetta & Ghetie, Science 2006; 313:308-309.*
Pearson H., Nature Mar. 17, 2006, Tragic Drug Trial Spotlights Potent Molecule, Nature News.*
Aspeslagh et al., Eur. J. Cancer 2016; 52:50-66.*
Sanmamed et al., Sem. Oncol. 2015; 24:640-655.*
C.L. Mackall, The Oncologist, 1999; 4:370-378.*
IB, "International Search Report and Written Opinion for Corresponding International Application No. PCT/US2014/066238", Feb. 4, 2015, pp. 1-11, Publisher: WIPO.
Vlad, G., et al., "Immunosupressive activity of recombinant ILT3. Int'l Immunopharmacology." 2006. vol. 6, pp. 1889-1894, Elsevier. ://www.elsevier.com/locate.
Colovai, A.I. et al., "Expression of Inhibitory Receptor ILT3 on Neoplastic B Cells is Associated with Lymphoid Tissue Involvement in Chronic Lymphocytic Leukemia." Cytometry Part B. Chemical Cytometry. Jan. 31, 2007. Clinical Cytometry Society. ://onlinelibrary.wiley.com/doi/10.1002/cyto.b.20164/pdf.
ISR. "Notification of Transmittal of the International Search Report and the Written Opinion of the International Searching Authority or the Declaration for PCT/US12/53714." Jan. 18, 2013.

* cited by examiner

*Primary Examiner* — Jessica H Roark
(74) *Attorney, Agent, or Firm* — Judith A. Evans; Timothy H. Van Dyke; Beusse Wolter Sanks & Maire

(57) ABSTRACT

The present invention relates to methods of using the expression of ILTL3 ligand or ILT3 on certain types of cancer cells as a diagnostic tool. Methods are provided for treating ILT3-ligand expressing cancers, such as T-cell acute lymphoblastic leukemia (T-cell acute lymphoblastic leukemia), for example by administering ILT3, the extracellular domain of ILT3 or ILT3Fc conjugated to a cytotoxic agent to kill the targeted cancer cell. Other methods are provided for treating cancers that express ILT3 on their surface, such as monocytic forms of AML, for example by administering anti-ILT3 antibodies conjugated to a cytotoxic agent.

3 Claims, 11 Drawing Sheets

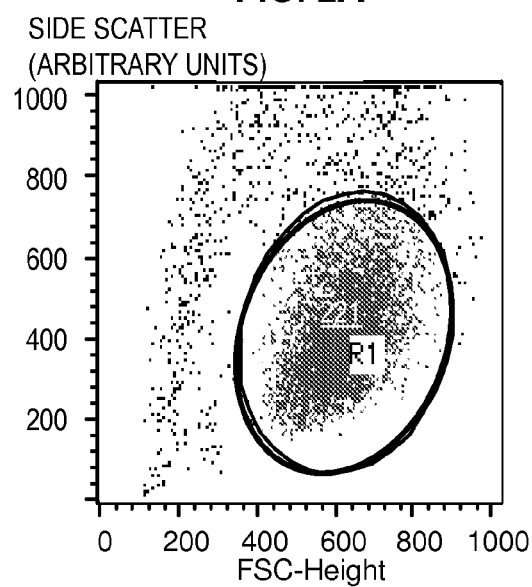 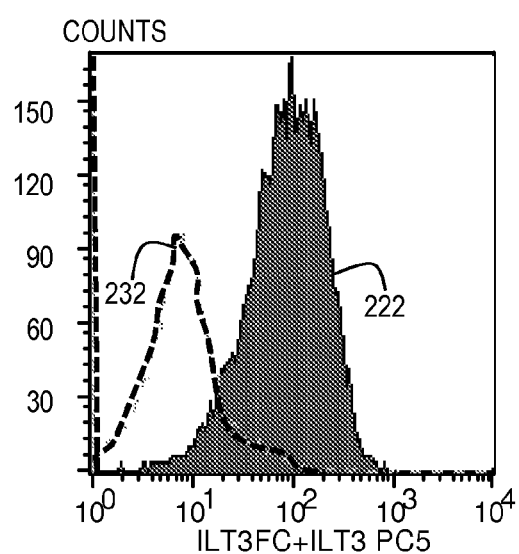

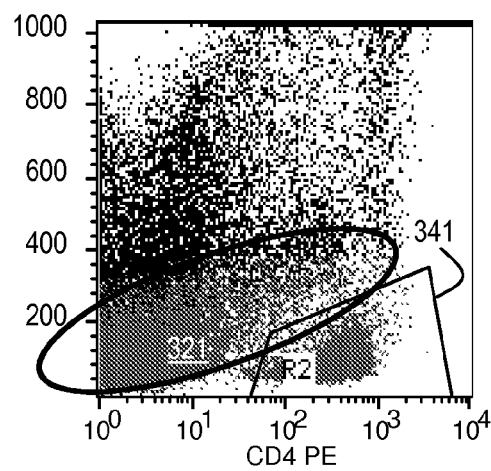 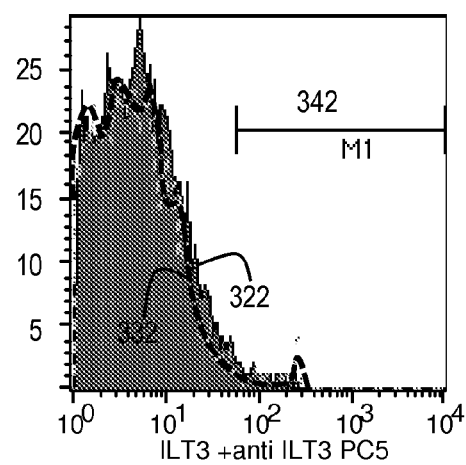
FIG. 3A
FIG. 3B

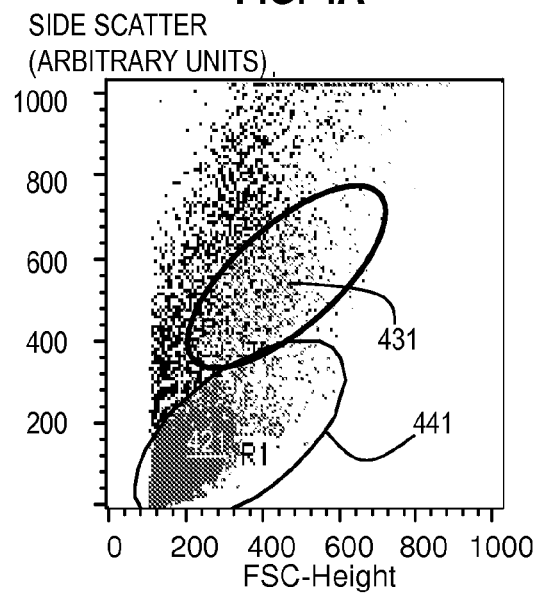
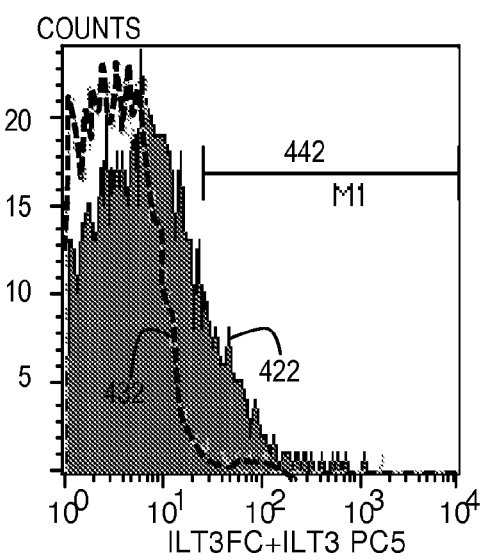

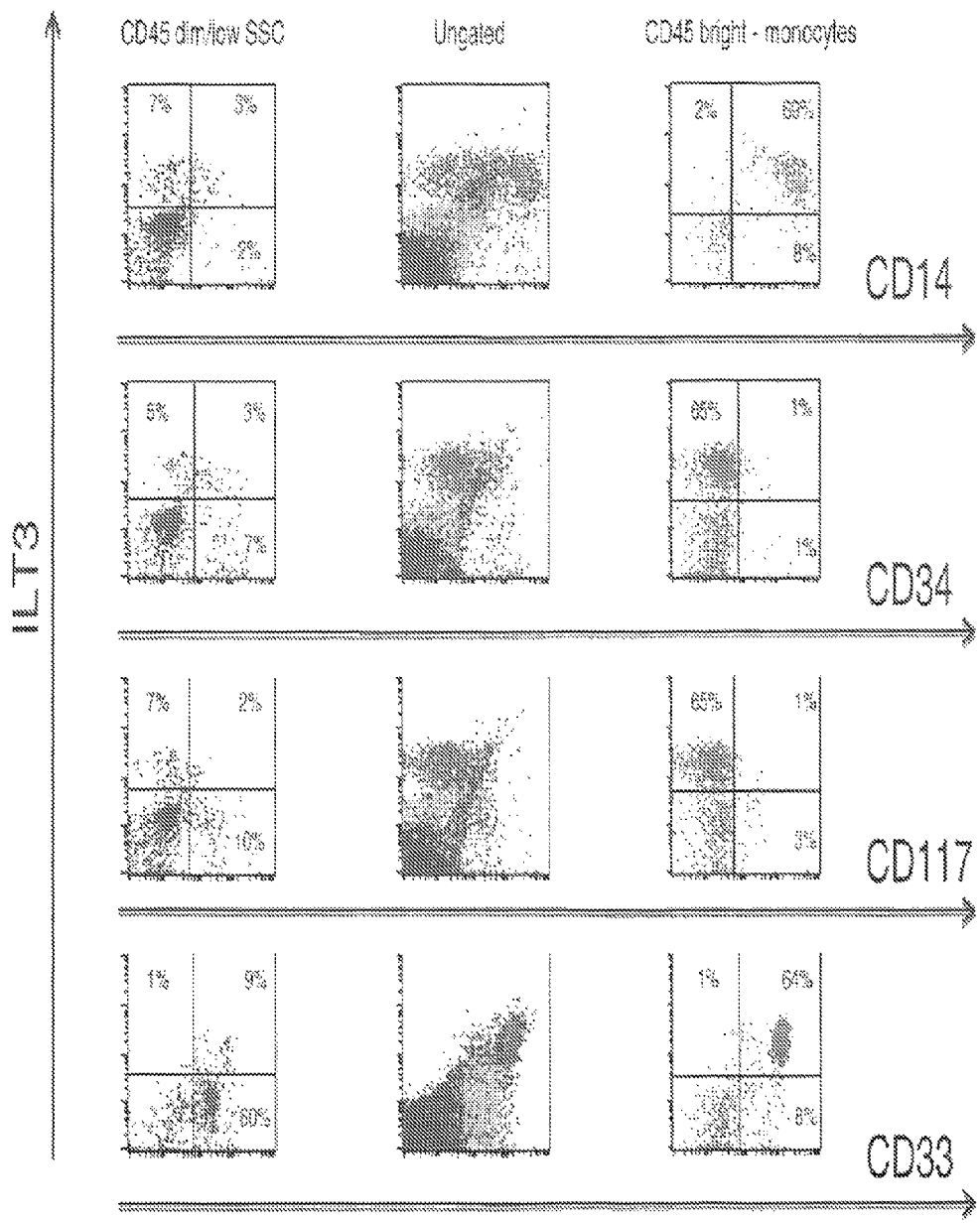

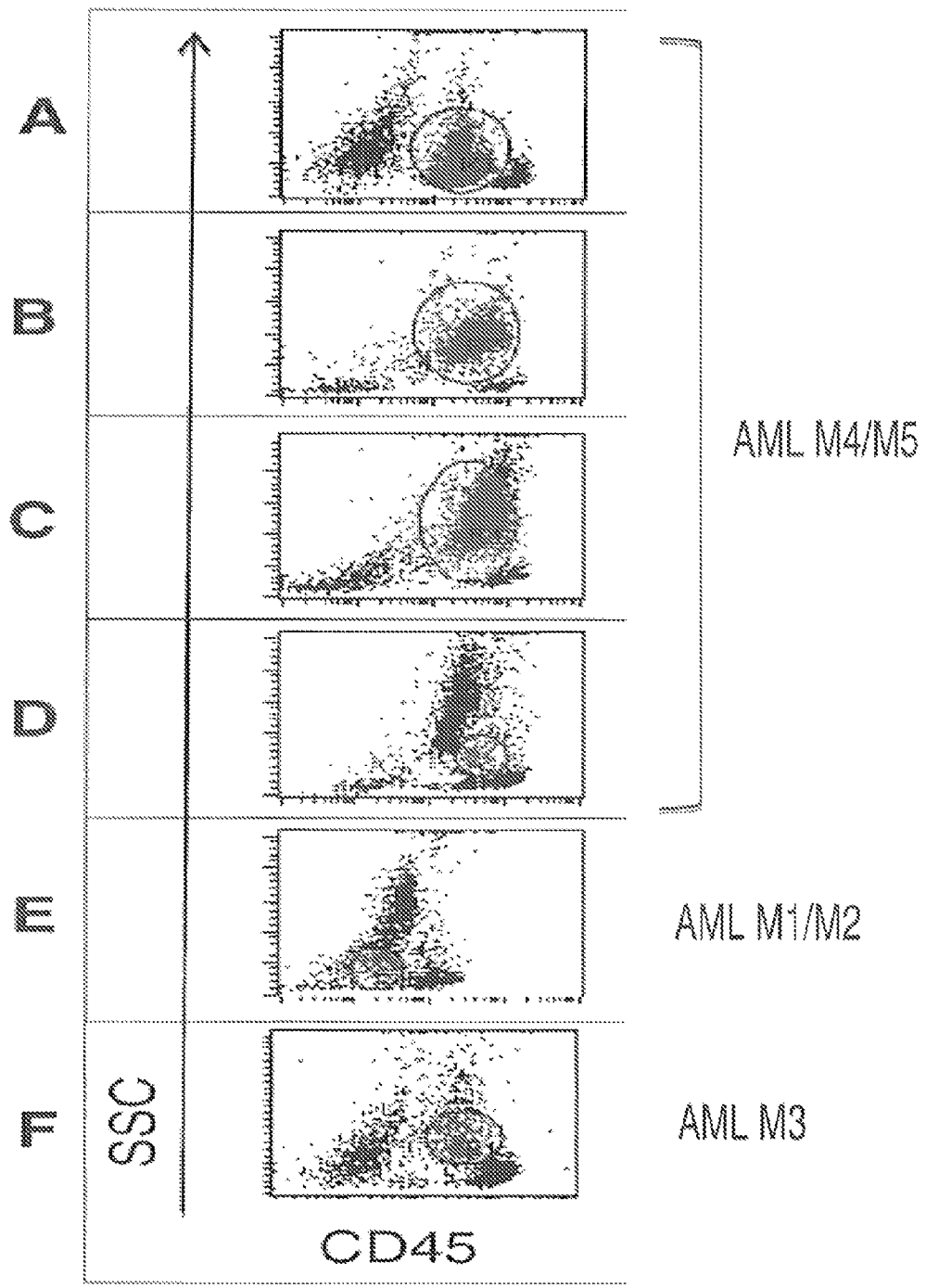

DIAGNOSIS AND TREATMENT OF CANCER EXPRESSING ILT3 OR ILT3 LIGAND

CROSS-REFERENCE TO RELATED APPLICATIONS

This application is a 371 national stage application that claims benefit of PCT/US 12/53714, filed Sep. 4, 2012, entitled, "Diagnosis and Treatment of Cancer Expressing ILT3 or ILT3 Ligand," and claims benefit of the following U.S. Provisional Applications 61/590,510, filed Jan. 25, 2012, entitled, "Diagnosis of Acute Lymphoblastic Leukemia" and, 61/530,936, filed Sep. 2, 2011, entitled, "Diagnosis and Treatment of Human Malignancies Using mAb Anti-ILT3 or ILT3Fc", the entire contents of which are hereby incorporated by reference as if fully set forth herein, under 35 U.S.C. §119 (e).

BACKGROUND OF THE INVENTION

Acute lymphoblastic leukemia (ALL) is a form of leukemia that is characterized by the presence of excess lymphoblasts due to the continuous multiplication of malignant immature white blood cells. ALL is a disease that rapidly progresses and is characterized by crowding of normal cells in the bone marrow due to the continuous multiplication of immature white blood cells.

Precursor T-cell acute lymphoblastic leukemia (T-ALL) causes 15% of acute leukemias in childhood, and approximately 40% of lymphomas in childhood. Acute refers to the relatively short time course of the disease, as it can be fatal in as little as a few weeks if left untreated. Most common in adolescent males, T-ALL's morphology is identical to that of precursor B-cell lymphoblastic leukemia. The rapid progression or relatively short time course of T-ALL without treatment makes early diagnosis extremely important since early intervention may delay onset of the disease and ultimately increase survival rates.

Currently no cellular markers specific for acute T-ALL are known, making diagnosis of the disease difficult. The only effective diagnostic method for acute T-ALL includes medical history, physical examination, complete blood count, and blood smears. There is an unmet need for the identification of cellular markers specific for acute T-ALL. The development of a diagnostic cellular marker that could aid in the diagnosis and treatment of T-ALL in its early stages is desirable.

Acute myeloid leukemia (AML) is one of the most common types of leukemia in adults (50), (51). Despite major advances in our understanding of the biology of AML, the 5-year survival of AML patients is only 20-40%. It has been proposed that AML originates from self-renewing hematopoietic stem cells (HSC)/progenitors that have acquired multiple genetic and/or epigenetic changes (52). These cells initiate a developmental hierarchy of single- or multiple lineage precursors exhibiting various degrees of maturation arrest. The heterogeneity of AML is evident from the wide variety of clinical manifestations, response to therapy, phenotypic features, and molecular and cytogenetic alterations (53), (54), (55). In clinical practice, the accurate diagnosis of AML subtypes is essential for risk stratification and treatment planning. The World Health Organization (WHO) and French American British (FAB) classification systems are currently used to subtype AML (50), (51), (56). Although the WHO classification system relies heavily on cytogenetic findings, these data are often not available at the time of diagnosis and initiation of treatment. Furthermore, the most frequent cytogenetic feature, which is identified in over 40% of the patients with AML, is the lack of any chromosomal alterations (57), (58). In patients with cytogenetically normal AML, specific gene mutations have been associated with certain AML subtypes (59), (60).

Therefore there is a need not only for better markers to distinguish the various forms of AML, but more specific treatments for the various forms of AML.

SUMMARY OF THE INVENTION

The present invention is based on the discovery that certain forms of cancer express ILT3 on their surface, including chronic lymphocytic leukemia (CLL) and AML with monocytic differentiation (AML m4/m5). Other forms of cancer have been discovered to express ILT3 ligand on their surface, such as T-ALL. Certain embodiments relate to methods and compositions for diagnosing and treating these forms of cancer.

In certain embodiments, cancers expressing ILT3 like CLL and AMLm4/m5 with monocytic differentiation are diagnosed and distinguished from noncancerous cells or other forms of cancer by binding to an anti-ILT3 antibody that is detectably labeled, or that can be detected by binding to a secondary reagent that is detectably labeled. Detectable labels for use in embodiments of the invention are described below. In an embodiment, diagnosing ILT3-expressing cancers includes (a) obtaining a biological sample from a subject that has or may have cancer that expresses ILT3 on the cancer cell surface, and a control sample from a normal subject; (b) contacting the subject and control samples with an anti-ILT3 antibody or a portion thereof that selectively binds to ILT3 under conditions that permit the probe to bind to the ILT3 expressed on the cancer cell surface; (c) determining the number or percentage of cancer cells that are bound to the antibody in the subject and control samples; and (d) determining that the subject has the ILT3-expressing cancer, if the number or percentage of cells bound to the antibody in the subject sample is significantly higher than the corresponding number or percentage of cells bound to the antibody in the control sample.

Certain embodiments are directed to treating these ILT3-expressing cancers by administering therapeutically effective amounts of an antibody that selectively binds to the ILT3 on the surface of the cancer cells (including newly discovered anti-ILT3 mAbs A, B, C and D described herein), which antibody is linked either to an isotope that emits radiation at a level that kills the cancer cell, or to a cytotoxic agent, thereby treating the subject for the cancer. An exemplary embodiment is a) identifying a subject in need of treatment for a cancer that expresses ILT3 on its surface, and b) administering therapeutically effective amounts of an antibody that selectively binds to the ILT3 on the surface of the cancer cells, which antibody is linked either to an isotope that emits radiation at a level that kills the cancer cell, or to a cytotoxic agent, thereby treating the subject for the cancer.

Other embodiments are directed to methods for diagnosing and distinguishing cancers that express ILT3 ligand on their surface such as T-ALL, from noncancerous cells or other forms of cancer by (a) obtaining a biological sample from a subject that has or may have cancer that expresses ILT3 ligand on the cancer cell surface, and a control sample from a normal subject; (b) contacting the subject and control samples with a probe that selectively binds to ILT3 ligand under conditions that permit the probe to bind to the ILT3 ligand on the cancer cell surface; (c) determining the number or percentage of cancer cells that are bound to the probe in the subject and control samples; and (d) determining that the subject has the ILT3 ligand-expressing cancer, if the number or percentage of cells bound to the probe in the subject sample is significantly higher than the corresponding number or percentage bound in the control sample. In certain embodiments the probe that selectively binds to ILT3 ligand is ILT3, ILT3Fc, the extracellular domain of ILT3 or an ILT3 ligand-binding fragment of one of these molecules.

In other embodiments cancers expressing ILT3 ligand on their surface, like T-ALL are treated by a) identifying a subject in need of treatment for a cancer that expresses ILT3 ligand on its surface, and b) administering therapeutically effective amounts of ILT3, ILT3Fc, the extracellular domain of ILT3 or a fragment thereof comprising the ILT3 ligand binding site, which ILT3, ILT3Fc, extracellular domain and fragment is linked either to a radioactive isotope that emits radiation at a level that kills the cancer cell or to a cytotoxic agent, thereby treating the subject for the ILT3 ligand-expressing cancer.

Cytotoxic agents for use in embodiments of the invention include Taxol®, *Pseudomonas* exotoxic fragment, cytocalasin B, gramicidin D, ethidium bromide, emetine, mitomycin, etopside, tenopside, vincristine, vinblastine, colchicin, doxorubicin, daunorubicin, dihydroxy antracin dione, mitoxantrone, mithramycin, actinomycin D, 1-dehydrotestosteron, glycocorticoids, procain, tetracaine, lidokaine, propranolol, and puromycin. Alternatively, the cytotoxic agent is the CD3 chain of the T cell receptor complex and whereby cancer cell lysis is induced by T-cell-mediated cytotoxicity against the cancer cell.

Other embodiments are directed to a diagnostic kit for the detection of cancer cells that express ILT3 on their surface, comprising an isolated monoclonal antibody or an ILT3-binding portion thereof according to claim 1; in another embodiment, the monoclonal antibody or portion thereof is detectably labeled either with a radioisotope or a label that can be visualized. Another embodiment includes a diagnostic kit for the detection of cancer cells that express ILT3 ligand on their surface, comprising ILT3, ILT3Fc, extracellular domain of ILT3, or an ILT3 ligand-binding fragment thereof. In an embodiment the ILT3, ILT3Fc, extracellular domain of ILT3, or the ILT3 ligand-binding fragment is detectably labeled either with a radioisotope or a label that can be visualized. Other embodiments are directed to newly discovered isolated anti-ILT3Fc monoclonal antibodies designated A, B, C or D or an ILT3-binding portion thereof, especially for use in embodiments of the invention to identify and treat cancer expressing ILT3.

BRIEF DESCRIPTION OF THE DRAWINGS

The present invention is illustrated by way of example, and not by way of limitation, in the figures of the accompanying drawings and in which like reference numerals refer to similar elements and in which:

FIG. 2(A)-(B) are graphs illustrating a T-ALL cell line expanded and maintained in culture.

FIG. 3(A)-(B) are graphs showing normal (resting) T cells from healthy individuals that express low or no ILT3 ligand. Specifically, CD4-gated T helper cells from a healthy blood donor indicate 1% ILT3Fc binding.

FIG. 4(A)-(B) are graphs demonstrating CD3-gated T cells from a healthy blood donor with 12% ILT3Fc binding.

FIG. 5. Flow cytometric analysis of whole bone marrow aspirate obtained from a patient with no evidence of hematological disease. FIG. 5(B) shows graphs of the data separated by CD45 brightness (increasing from dim on left to bright on right, with the remainder, called ungated, in the middle). The data are also separated by side scattering (SSC) levels, with higher levels in the graphs at the top and lower levels in graphs at the bottom. Cells were gated in the CD45 versus side scatter plot as follows: Lymphocytes—CD45bright/low SSC, Monocytes—CD45bright/intermediate SSC, Granulocytes—CD45dim/high SSC, Precursor cells—CD45dim/low to intermediate SSC. Cell surface expression of ILT3 and CD 14, or CD33, CD34 or CD 117 is depicted. The results are representative for the immunophenotypic profile observed in 20 non-involved bone marrow samples.

FIG. 7. A flow cytometric analysis of whole bone marrow aspirates obtained from patients with AML. Leukemic cells were gated based on abnormal immunophenotypic and light scatter features. The results are representative for: AML m4/m5 (M4/M5—Panels A-D), AML without differentiation (M 11M2—Panel E), and APL (M3—Panel F). Cell surface expressions of ILT3, CD14, CD34, CD45 and CD117 are depicted. FIG. 7(A) are graphs that show results for CD45 vs SSC in the various panels.

Figure 1A:
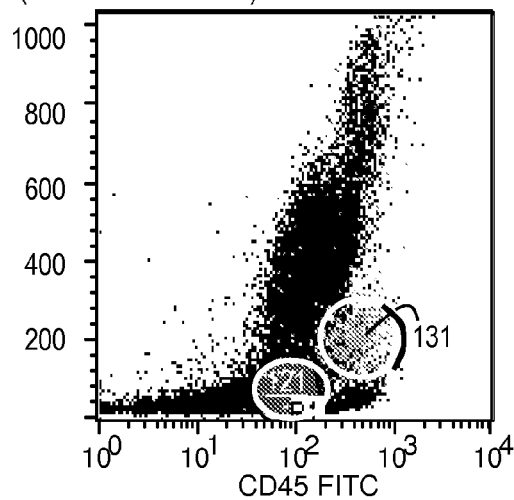
FIG. 1(A)-(B) are graphs demonstrating bone marrow aspirate from a patient with T-ALL (CD45 dim gate identifies leukemic cells).
Figure 1B:
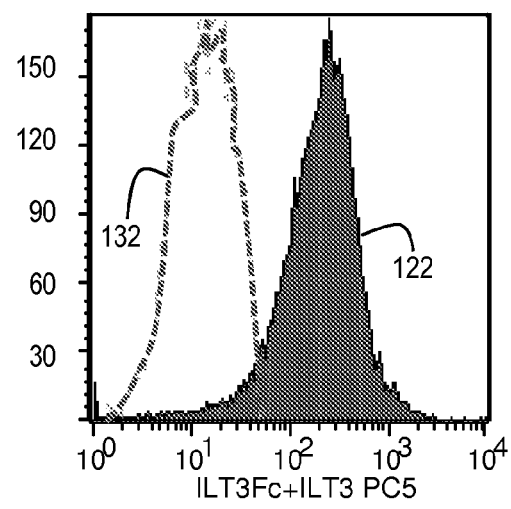

In the Summary of the Invention above, in the Detailed Description of the Invention, and the claims below, as well as the accompanying figures, reference is made to particular features of the invention. It is to be understood that the disclosure of the invention in this specification includes all possible combinations of such particular features. For example, where a particular feature is disclosed in the context of a particular embodiment or embodiment of the invention, or a particular claim, that feature can also be used, to the extent possible, in combination with and/or in the context of other particular embodiments and embodiments of the invention, and in the invention generally. For the purposes of explanation, numerous specific details are set forth in order to provide a thorough understanding of the present invention. It will be apparent, however, to one skilled in the art that the present invention may be practiced without these specific details.

DETAILED DESCRIPTION OF THE INVENTION

The practice of the invention will employ, unless otherwise indicated, conventional techniques of molecular biology (including recombinant techniques), microbiology, cell biology, biochemistry, and immunology, which are within the skill of the art. Unless defined otherwise, technical and scientific terms used herein have the same meaning as commonly understood by one of ordinary skill in the art to which this invention belongs.

It has been discovered that cancer cells of AML type with monocytic differentiation (AML m4/m5) expresses ILT3 on their surface. Cancer cells of another form of cancer, the T-ALL form, have been discovered to express ILT3 ligand on their surface. Certain embodiments relate to methods and compositions for diagnosing and treating these different forms of cancer; those that express ILT3 and those that express ILT3 ligand.

I. DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference.

Generally, nomenclatures used in connection with, and techniques of, cell and tissue culture, molecular biology, immunology, microbiology, genetics, protein, and nucleic acid chemistry and hybridization described herein are those well-known and commonly used in the art. The methods and techniques of the present invention are generally performed according to conventional methods well known in the art and as described in various general and more specific references that are cited and discussed through the present specification unless otherwise indicated. Many references are available to provide guidance in applying the above techniques (Kohler et al., Hybridoma Techniques (Cold Spring Harbor Laboratory, New York, 1980); Tijssen, Practice and Theory of Enzyme Immunoassays (Elsevier, Amsterdam, 1985); Campbell, Monoclonal Antibody Technology (Elsevier, Amsterdam, 1984); Hurrell, Monoclonal Hybridoma Antibodies: Techniques and Applications (CRC Press, Boca Raton, Fla., 1982); and Zola, Monoclonal Antibodies: A Manual of Techniques, pp. 147-158 (CRC Press, Inc., 1987)). Northern blot analysis is a conventional technique well known in the art and is described, for example, in Molecular Cloning, a Laboratory Manual, second edition, 1989, Sambrook, Fritch, Maniatis, Cold Spring Harbor Press, 10 Skyline Drive, Plainview, N.Y. 11803-2500. Typical protocols for evaluating the status of genes and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis).

"AML with monocytic differentiation" hereafter "AMLm4/m5" means subtypes of acute myeloid leukemia that comprise over 10% of AML cases and occurs in all age groups. They have been found frequently associated with deletions and translocations involving 11q23, inv(16) and t(9,11), and may also harbor t(6,9), inv(3), NPM1 or FLT3-ITD mutations. Monocytic differentiation is identified by morphology and confirmed by cytochemical stains or flow cytometry.

"Antibody-linked cytotoxic agent" means a monoclonal antibody (mAb) that is linked, conjugated, or otherwise bound to a cell-killing drug to be used as vehicle to target cancer cells due to the high binding specificity.

"Biological sample" means a variety of sample types obtained from an organism and can be used in the embodiments of the herein described diagnostic or monitoring assays. The sample is selected from any part of a patient's body, including, but not limited to, blood, lymph nodes, spleen, or bone marrow aspirates. Preferred samples for diagnosing cancers that express ILT3 or ILT3 ligand are blood (including plasma and serum), bone marrow aspirates, fine needle aspirates, body fluids (such as pleural fluid, cerebro-spinal fluid). The term encompasses samples that have been manipulated in any way after their procurement, such as by treatment with reagents, solubilization, or enrichment for certain components. The term encompasses a clinical sample.

"ILT3" means "Immunoglobulin-Like Transcript-3", and is synonymous with "ILT-3", "LIR-5", "CD85K" and "LILRB4." The mRNA coding sequence for human ILT3 is provided under GenBank No. U82979. Human ILT3 is a transmembrane protein having 447 amino acids with a predicted molecular mass of about 47 kD. ILT3 behaves as an inhibitory receptor when cross-linked to a stimulatory receptor. ILT3 has an extracellular region that includes N-terminal amino acids 1-259 and a signal peptide of amino acids 1-16; a transmembrane domain that includes amino acids 260-280; and a cytoplasmic domain that includes amino acids 281-448. ILT3 has cytoplasmic domain which includes an ITIM motif at amino acids 412-415 and 442-445. The extracellular domain of contains two Ig domains. "ILT3" shall mean the gene, mRNA, or protein of "Immunoglobulin-Like Transcript-3", and is synonymous with "ILT-3", "LIR-5", "CD85K" and "LILRB4". The mRNA coding sequence for human ILT3 is provided under GenBank No. U82979.

The "extracellular domain of ILT3" or "ED" means the N-terminal 258 amino acid residues of ILT3 (e.g., human ILT3 having the sequence of GenBank Accession No. U82979). The extracellular domain of contains two Ig domains, one or both of which are likely to contribute to the ILT3 ligand binding. The extracellular domain of ILT3 includes, for example, the IgG1-like domain 1 (residues 42-102 of human ILT3), the IgG1-like domain 2 (residues 137-197 of human ILT3), and the N-terminal 250, 240, 230, 220, 210, 200, 190, 180, 170, 160 or 150 amino acid residues of ILT3.

"ILT3 Ligand" means the molecule expressed on the surface of T-cells and certain cancer cells such as T-ALL cells to which ILT3, ILT3-FC and certain fragments thereof selectively bind. The ILT3 ligand is expressed transiently on the surface of up to about 10-30% of normal T cells from peripheral blood monocytes (PBMC) which have been allo-activated by exposure to HLA mismatched cells. The ligand-binding site on ILT3 is in the extracellular domain of ILT3.

"Specific binding of antibodies" means that the antibodies: 1) exhibit a threshold level of binding activity, and/or 2) they do not significantly cross-react with known related polypeptide molecules.

"Specific binding" of an agent, such as the ILT3 ligand-binding probe means that the agent binds to the target protein, such as ILT3 ligand, with greater affinity than it binds to unrelated antigens.

"ILT3Fc" means the extracellular domain of human ILT3 (ED) operably affixed to the Fc portion of an immunoglobulin. In an embodiment the Fc portion comprises a function-enhancing mutation, such as a mutation that inhibits the binding of the Fc portion of an immunoglobulin to an Fc receptor. In an embodiment the Fc portion derived from human IgG1. In one example, the function-enhancing mutation in the Fc portion of the immunoglobulin is an Asn→Gln point mutation at amino acid residue 77 of the Fc portion of human IgG1. The Fc portion of ILT3Fc may be substituted with any other peptide that promotes dimerization or oligomerization of the probe or otherwise stabilizes the probe. For example, the peptide may comprise cysteine residues that form disulfide bonds or other residues that promote covalent or nonconvalent interactions between the peptides such that the peptides mediate dimerization or oligomerization. Exemplary oligomerization domains are described in, e.g., WO 00/69907, WO 99/62953, WO 98/56906, WO 98/18943, and WO 96/37621.

"ILT3 probe" and "ILT3 ligand-binding probe" are used interchangeable to mean a molecule that selectively binds to ILT3 ligand. The ILT3 ligand-binding probes include full-length ILT3, the extracellular domain (ED) of ILT3, the recombinant protein (ILT3Fc), and fragments of ILT3 that include the ED. The probes can be used alone or they can be bound to a compound that stabilizes the probe or increases binding of the probe to the targeted ILT3 ligand. Since there is a high level of sequence homology among various species, the ILT3 ligand-binding probes, though preferably including or derived from human ILT3, can come from any species as long as it selectively binds to ILT3 ligand on a targeted cancer cell or T-cell.

"A probe for detecting ILT3" means a molecule that specifically binds to ILT3 that is expressed on the surface of a cancer cell, such as an AML cancer cell of monocytic lineage. Such probes include anti-ILT3 mono- or polyclonal antibodies, or an antigen (ILT3)-binding portion thereof.

"Detectable probe" means a probe for use in the diagnostic methods described herein, that may be detected or visualized using well known methods such as radioactive isotopes such as $^{125}I$, $^{32}P$, $^{35}S$, and $^{3}H$, enzymes, chemiluminescent agents, and fluorescent dyes. Different types of chemical labels or tags can be conjugated to secondary or primary antibodies against ILT3 or ILT3Fc to facilitate their visualization (i.e., detection and measurement.) The choice of label or tag depends on the sensitivity required, ease of conjugation with the probe, stability requirements, and available instrumentation.

"Immunoglobulin" and "antibody" are used synonymously herein, and include any anti-ILT3 antibody that has high affinity for ILT3, including those antibodies that have high affinity for the extracellular domain of ILT3. In the context of the invention, anti-ILT3 antibodies are administered therapeutically to target delivery of a cytotoxin to a cancer cell expressing ILT3 on its surface (such as AML m4/m5). For diagnostic use, the anti-ILT3 antibodies selectively bind to ILT3 expressed on the surface of a cancer cell such as AML m4/m5. Included, by way of example, are both naturally occurring and non-naturally occurring antibodies, polyclonal and monoclonal antibodies, any antigen-binding fragments (e.g., Fab fragments, as opposed to Fc fragments) thereof, chimeric antibodies (e.g., humanized antibodies) and wholly synthetic antibodies, and antigen-binding fragments thereof. Within the scope of the term "antibody" are antibodies that have been modified in sequence, but remain capable of specifically binding to ILT3, ILT3Fc or the ED or fragment of ILT3 comprising the ED. In some embodiments anti-ILT3 antibodies are used as secondary reagents to label ILT3 (used as a probe) that binds to ILT3 ligand. Examples of modified antibodies include interspecies chimeric and humanized antibodies; antibody fusions; and heteromeric antibody complexes, such as diabodies (bispecific antibodies), single-chain diabodies, and intrabodies (see, e.g., Marasco (ed.), Intracellular Antibodies: Research and Disease Applications, Springer-Verlag New York, Inc. (1998) (ISBN: 3540641513), the disclosure of which is incorporated herein by reference in its entirety).

By "French American-British (FAB) subtypes" is meant the FAB subtypes M4, M5a and M5b" of AML that are morphologically characterized by monocytic differentiation. These subtypes show distinct clinical features, such as high risk of extramedullary disease, high leukocyte count, and coagulation abnormalities. AML with monocytic differentiation comprises (herein AML m4/m5) over 10% of AML cases and it occurs in all age groups.

The terms "individual," "subject" and "patient," are used interchangeably herein and refer to any human subject for whom diagnosis, treatment, or therapy is desired.

"Operably affixed" or "bound to" or "linked to" or "conjugated to" with respect to the connection between a probe (an ILT3 ligand-binding probe that includes ILT3, ILT3Fc and the ED, or a probe for detecting ILT3 such as an anti-IL3 antibody) and the label, or the probe and Fc, for example, shall mean affixed (e.g., via peptide bond) in a manner permitting the ILT3 ligand-binding probe to bind to the ILT3 ligand on the surface of T-cells or for an anti-ILT3 antibody to bind to ILT3. In one embodiment, a polypeptide linker of 10, 11, 12, 13, 14, 15 or 16 amino acid residues in length is used to join the ILT3 and Fc moieties.

"Polypeptide" and "protein" are used interchangeably herein, and each means a polymer of amino acid residues. The amino acid residues can be naturally occurring or chemical analogues thereof. Polypeptides and proteins can also include modifications such as glycosylation, lipid attachment, sulfation, hydroxylation, and ADP-ribosylation.

"Selectively binds" and "specifically binds" are used interchangeably to mean the specific or preferential affinity with which two or more proteins interact such as an antibody or a protein with a substrate. A labeled ILT3 ligand-binding probe may specifically bind to the T-ALL biomarker ILT3 ligand.

"Significantly higher" with respect to the level of detectably labeled T-cells or cancer cells means about one standard deviation above the mean of a normal population, which may vary depending on the sample size of the normal and cancer populations and the type of cancer.

In the following description, for the purposes of explanation, numerous specific details are set forth in order to provide a thorough understanding of the present invention. It will become apparent, however, to one skilled in the art that the present invention may be practiced without these specific details.

II. OVERVIEW

The inhibitory receptor ILT3 is a member of the immunoglobulin-like transcript (ILT, LIR or LILR) family and is expressed by dendritic cells, monocytes, endothelial cells and osteoclasts, but not T lymphocytes (47), (48), (49). Encoded in the leukocyte receptor cluster on human chromosome I9, the ILT proteins are structurally and functionally related to the killer cell immunoglobulin-like receptors (KIR) and deliver either activating or inhibitory signals (50), (51), and (52). Inhibitory ILT proteins display intracytoplasmic ITIM motifs that recruit SHP-1 phosphatases that contribute to downstream inhibitory signals. In contrast, activating ILTs have short cytoplasmic tails and associate with adaptor proteins, such as FceRIg, to activate cell signaling.

The function of ILT3 proteins expressed by antigen-presenting cells (APC), such as monocytes and dendritic cells, has been described (53), (54), (55), (56). For example, dendritic cells expressing high levels of inhibitory receptors ILT3 and ILT4 were shown to induce anergy of CD4+ T helper cells and differentiation of CD8+ T suppressor cells (53), (54), and (51). On the other hand, knockdown of ILT3 renders dendritic cells more sensitive to Toll like receptor (54). Although absent on normal B lymphocytes, ILT3 is expressed by leukemic B cells from a subset of CLL patients displaying extensive lymph node involvement. Expression of ILT3 by hematopoietic precursors has not been yet characterized. It has now been discovered that ILT3 is selectively expressed on AML of monocytic differentiation.

U.S. application Ser. No. 12/072,119, entitled ILT3 and ILT4-Related Compositions and Methods, discloses a means for treating cancer by removing sILT3 from the blood either and then returning cleansed blood to the patient in order to increase the immune response to a disease such as a viral disease or cancer. This method can further include administering an anti-sILT3AB to neutralize sILT3. However, there is no recognition of that there is any form of cancer that expresses ILT3 on its surface, nor is there a disclosure or suggestion that an anti-ILT3 antibody could be conjugated to a toxic agent to kill a cell, such as a cancer cell that expresses ILT3. Moreover, while ILT3 on the surface of a cancer cell could bind the anti-ILT3 mAb, this alone is not enough to kill a cancer cell. (Chang et al. Nat Immunol 2002).

In PCT/US02/20128 entitled ILT3 and ILT4-Related Compositions and Methods, a method for treating cancer by administering an anti-ILT3 antibody is disclosed. It explains that "the inhibitory function of ILT3 and ILT4 receptors concerns the central control mechanisms of the immune response which must be inhibited to induce specific tolerance in transplantation and autoimmune diseases and augmented [the immune response] in AIDS and Cancer." Nowhere does it suggest that an anti-ILT3 antibody can bind to a cancer cell itself, nor does it suggest administering an anti-ILT3 antibody conjugated to a cytotoxic agent to kill the targeted ILT3-expressing cancer. Instead, this application discloses methods that enhance the immune response by blocking immune suppression by neutralizing ILT3 thereby permitting the cancer patient to mount a stronger immune response to the cancer.

ILT3-Ligand Expressing Cancers

It is known that the ILT3 ligand (herein "ILT3 ligand" or "ILT3L" or "the ligand") is expressed on the surface of certain cells. However, the sequence or chemical identity of the ILT3L has not yet been identified and so it is not yet possible to generate antibodies that selectively bind to the ligand. The ILT3 ligand by definition, selectively binds to the inhibitory receptor ILT3. It is also known that the ligand-binding site on ILT3 is in the extracellular domain of ILT3. Further, ILT3 ligand is expressed transiently on the surface of up to about 15% of normal T cells.

It has now been discovered that the ILT3 ligand is constitutively and selectively expressed at high levels on at least 50% and typically 90% of malignant T-ALL cells harvested from patients known to have the disease, as well as in T-ALL cell lines. As is discussed below, this discovery is the basis of new methods for diagnosing and treating T-ALL and any other cancer that is discovered to express ILT3-ligand on its surface.

ILT3-Expressing Cancers

Immunohistochemical analysis is often used to subtype AML yet its value in the diagnosis of AML with monocytic components is limited by the lack of highly sensitive and specific monocytic markers (40). (41). Several markers are being used for ascertaining monocytic differentiation by flow cytometry, e.g. CD4, CD11c, CD14, CD36 and CD64 (44), (45), (46). Although the expression of these markers by the leukemic cells is helpful for lineage assignment, the diagnosis of AML m4/m5 remains challenging.

The French American-British (FAB) subtypes M4. M5a and M5b that distinguish AMLm4/m5 with monocytic differentiation, show distinct clinical features, such as high risk of extramedullary disease, high leukocyte count, and coagulation abnormalities (36), (37). AMLm4/m5 comprises over 10% of AML cases and it occurs in all age groups (25), (36), and (39). Certain trans locations, such as t(9, 11) and 16q22, involving the mixed lineage leukemia (MLL) and the core binding factor beta genes, respectively, are commonly seen in monocytic leukemias (26), (33). Mutations of the nucleophosmin (NPM1) gene have been also associated with myelomonocytic or monocytic morphology and are predictive of favorable outcome (30). However, these abnormalities are not absolutely specific for the monocytic lineage and identify only a fraction of patients with AML displaying monocytic differentiation.

It has now been discovered that ILT3 is expressed by normal and leukemic myeloid precursor cells, and that ILT3 expression is therefore a biomarker for identifying normal hematopoietic precursors committed to the monocytic lineage and for distinguishing AML m4/m5 from other types of AML. It has also been previously shown that ILT3 is a useful marker for identifying (CLL) (57). This discovery is the basis for new methods for diagnosing and treating AML and CLL cancers that express ILT3, and any other cancer that is discovered to express ILT3 on its surface.

III. RESULTS

ILT3 Ligand is Constitutively and Selectively Expressed at High Levels on Malignant T-ALL Cells 12/12 T-ALL patients exhibited ILT3 ligand expression on malignant leukemic cells in a blood sample. Malignant leukemic cells were clinically diagnosed as such using flow cytometry, cytopathology and karyotyping and identified by in flow cytometry experiments by the CD45-dim/negative expression and low SSC profile. In one of the 12 patients, the ligand was expressed on 50% of the malignant T-ALL cells, but in the other 11 patients the ligand was expressed on 90% of the T-ALL cells. By contrast, only a small fraction of normal T-cells expressed the ligand (about 15%). Based on this discovery, the ILT3 ligand is a clinically useful biomarker for diagnosing patients who have T-ALL. The expression of ILT3 ligand also differentiated T-ALL from other forms of leukemias.

In view of this discovery, a set of embodiments is directed to a method for diagnosing ILT3 ligand-expressing cancers including T-ALL in a patient by determining if a biological sample taken from a patient includes malignant T-ALL cells that express ILT3L at significantly higher levels that T-cells from a normal control patient. By significantly higher is meant that the number or percentage of ILT3 ligand-expressing T cells in a patient is about one standard deviation or more above the mean seen in a normal patient or population of normal patients.

In an embodiment, this diagnosis of T-ALL is determined by obtaining a biological sample from a patient suspected of having T-ALL and another sample from a normal subject; contacting the T-cells in a test sample from the patient and in a control sample from the normal subject, with detectably labeled ILT3 ligand-binding probe (such as ILT3, the ED of ILT3, or preferably fluorescently labeled ILT3Fc); determining the number [or percentage] of ILT3 ligand-positive T-cells in each sample, and determining that the patient has T-ALL if the number [or percentage] of labeled T-cells labeled in the test sample is significantly higher (at least about 1 standard deviation above normal) than the corresponding number or percentage detected in the control sample. In the example samples from 12 patients used for this study significantly higher labeling was about 15% higher in T-ALL patients than in normal patients. This actual percentage used in a particular embodiment may change based on sample size of the normal and cancer populations and on the type of cell expressing ILT3.

In an embodiment, the detectable label on the ILT3, ED, or ILT3Fc probe is a fluorophore and the amount of label bound to the T-cells in the test and control samples of step (d) above is determined using flow cytometry. The method may further comprise quantifying the amount of fluorescence emitted from each fluorophore-labeled T-cell, for example, using flow cytometry.

In some embodiments of the method, the ILT3 ligand-binding probe (ILT3, ILT3Fc, or ED or fragment thereof) is indirectly labeled with a secondary reagent such an anti-ILT3 antibody (monoclonal, polyclonal, or chimeric antibody) that is detectably labeled. Further details of the assay where the probe is indirectly labeled are illustrated by non-limiting Example 1. Four new anti-ILT3 monoclonal antibodies have been discovered and are herein referred to as anti-ILT3 mAb A, B C and D. Certain embodiments of the invention are directed to these new anti-ILT3 mAbs and their diagnostic use for example to detect ILT3-ligand expressing cancer cells. In such an embodiment the ILT3 ligand complexes with ILT3. ILT3Fc or ED probes, and the anti-ILT3 antibodies bind to the probe. In some embodiments discussed below, the anti-ILT3 mAbs are conjugated to cytolytic/cytotoxic agents in order to kill ILT3-expressing cancer cells such as AML and CLL. In other embodiments the anti-ILT3 mAb are detectably labeled and used to diagnose cancers that express ILT3 on their surface, such as T-ALL and CLL.

Typical labels for use in detecting proteins and antibodies include labeling a protein or antibody for detection or visualization using radioactive isotopes, enzyme substrates, metal complexes, haptens, co-factors, ligands, colorimetric agents, dyes, and chemiluminescent or fluorescent agents that can be bound to the protein or antibody. The fluorescent agents are selected from the group comprising 6-FAM™, Acridine, Alexa dye, e.g., Alexa 488, Alexa Fluor, AMCA, BODIPY, Cascade Blue, Cholera toxin B, Cy2, Cy3, Cy5, Cy5.5, Cy7, Dabcyl, Dansyl derviatives, Diamidino yellow, Dy 750, Edans, Eosin, Erythrosin, Fast blue, Fluorescein isothiocyanate, Green fluorescent protein (GFP) and derivatives, HEX™, Horseradish peroxidase, Hydroxystilbamidine, Iowa Black®, IRDye® Joe, LightCycler 640, MAX 550, Oregon Green, Phycoerythrin, Pseudorabies virus, Red Leuco dye, 3,3',5,5'-tetramethylbenzidine (TMB), Rhodamine and its derivatives, e.g., Rhodamine Green™ and Rhodamine Red™, Rhodol Green, ROX™, TET™, TEX 615, Texas Red®, TYE (including TYE™ 563, TYE™ 665, TYE™ 705), Umbelliferone, WellRED™ D2, WellRED™ D3, WellRED™ D4 and TAMRA dyes (such as pyrene, TAMRA, FITC), or combinations thereof. GFP was used in the experiments described herein, however there are now many different mutants of GFP (e.g., see Shaner N. Steinbach P, Tsien R "A guide to choosing fluorescent proteins" (PDF). *Nat Methods* v2 (12), pp 905-9, 2005). Methods for labeling and guidance in the choice of labels appropriate for various purposes are discussed, for example in Sambrook et al., *Molecular Cloning: A Laboratory Manual*, CSHL, New York, 1989; and Ausubel et al. *Current Protocols in Molecular Biology*, John Wiley & Sons, New York, 1998.

Direct labeling methods include radioisotope labeling. Radiolabels include, but are not limited to $^{131}I$, $^{14}C$, $^{45}Ca$, and $^{3}H$, $^{125}I$, $^{32}P$ and $^{35}S$. Indirect labeling methods include binding fluorescent tags, or biotin complexes (which can be bound to avidin or streptavidin), or peptide or protein tags. Visual detection methods include colorimetric agents, dyes, chemiluminescent or fluorescent agents, or with horse radish peroxidase, alkaline phosphatase and the like. Any label that can be detected can be used to quantify binding of Fluor the ILT3 ligand-binding probe (comprising ILT3, or ILT3Fc or ED) to ILT3 ligand on T-cells. Fluorophores are typically operably affixed, bound or otherwise attached to the probe or the secondary reagent.

When the identity of the ligand is discovered, then antibodies that bind to the ligand can also be labeled and used to identify T-ALL cells.

Other embodiments provide a method of assessing whether a T-ALL patient is responsive to treatment by determining the number of T cells that are detectably labeled in a patient sample prior to treatment and after treatment, and then determining that the patient is responding to treatment if the number of delectably labeled T-cells in the pre-treatment sample is significantly higher than the number of delectably labeled T-cells in the post-treatment sample.

ILT3 is Constitutively Expressed on Malignant Leukemia aml Cells of Monocytic Differentiation The results described herein regarding AML, show that ILT3 is a highly specific and sensitive biomarker that is constitutively expressed by normal and leukemic myeloid precursors. Thus, ILT3 can be used as a diagnostic tool for distinguishing AML m4/m5 from other types of AML.

The key results show:

Flow cytometric analysis of AML samples (including AML with and without monocytic differentiation) from patients with non-involved bone marrow indicated that 80±9% of the CD14+ monocytes were ILT3+. Granulocytes were essentially negative.

No significant difference was found between the frequency of ILT3+ precursor cells identified in bone marrow samples obtained from patients previously treated for AML who are currently disease free (N=13) and from non-AML controls (N=7).

Flow cytometric analysis of samples from patients with AML with or without monocytic differentiation showed that ILT3 was variably expressed by the leukemic cells (range 1-99%; mean±STD, 44.±41%).

The frequency of ILT3+ cells in patients with AML m4/m5(AML/m4/m5) was dramatically elevated compared to patients with AML that does not have monocytic differentiation (AML/m1m2m3) Specifically 65±33% of the cells in AML/m4/m5 were ILT3+, versus 1±1% in AML/m1/m2/m3 (p<0.0001). This means that essentially all of the ILT3+ cells in AML/m4/m5 samples fell above one standard deviation above the mean for AML/m1/m2/m3 samples. Based on this, a threshold of 10 to 15% was chosen, such that if more than about 10-15% of the cells in the sample are ILT3+, the sample is identified as AML/m4/m5 (ILT3+>10%; p<0.0001); if less than about 10% to 15% or less of the cells in the sample are ILT3+, the sample is not identified as AML/m4/m5. Using this threshold, it was discovered that all of the 18 cases so determined to be AML/m4/m5 agree with those 18 cases that were previously identified as AML/m4/m5 analyzed using established morphological, immunohistochemical and cytogenetic criteria to determine the AML type.

CD11c, CD33, and HLA-DR were positive in >90% of the malignant leukemic cells from patients having AML M4/M5. By contrast, CD11c and CD33 were positive in >50% and 100%, respectively, of leukemic cells from patients with AML M1/M2 and M3. HLA-DR was positive in >80% of patients with AML MI/M2.

CD14 was only expressed in 2 of 18 cases (61%) of AML m4/m5.

Co-expression of ILT3 and CD117 was observed in 50% of cases with AML m4/m5, while co-expression of ILT3 and CD34 was 39%.

Flow cytometric results obtained after allogeneic stem cell transplantation in a patient treated for AML m4/m5 indicated ILT3+ staining and highlighted a population of monocytic precursors that accounted for 64% of the CD45dim/low SSC cells (4% of all nucleated cells).

ILT3+ AML M4/M5 cells co-expressed CD4, CD11c, CD33, CD34, CD64, CD117, and HLA-DR, but they were negative for CD14, a phenotype consistent with that of the original leukemia.

Cytogenetic data indicate that 27 of 32 patients with AML M4/M5 carried chromosomal abnormalities including a 5q deletion, monosomies of chromosomes 5 and/or 7, and complex karyotypes (>3 unrelated abnormalities). One or more abnormalities were detected in 5 of 17 patients with AML that does not have monocytic differentiation (M1, M2, M3). None were detected in any of the patients with ILT3+ AML M4/M5 (p=0.046).

Most of the cytogenetic abnormalities associated with a favorable prognosis were found in the AML M3 (APL) group. Seven out of 10 patients from this group carried the t(15, 17) abnormality.

Cytogenetic abnormalities previously associated with monocytic differentiation, namely t(9, 11) and 16q22, were observed in only 3 of 14 patients with AML M4/M5.

Cytogenetic abnormalities previously associated with monocytic differentiation, namely t(9, 11) and 16q22, were observed in only 3 of 14 patients with AML M4/M5.

Construction of Human ILT3

Methods for making, isolating and purifying human ILT3, the soluble ILT3 extracellular domain and other fragments of ILT3, or for making ILT3Fc using, for example, recombinant technology or chemical synthesis, are described in detail in Cosman, U.S. Pat. No. 6,448,035. Cosman also describes variants, homologs and analogs of the ILT3 extracellular domain and methods for making, identifying and isolating anti-ILT3 antibodies.

Purified polypeptides comprising ILT3 or the extracellular domain of human ILT3 can be used as the ILT3 ligand-binding probe in embodiments of the present invention because this domain is known to contain the ILT3 ligand-binding site. The polypeptides may be purified from recombinant expression systems (by subcloning the nucleic acid encoding the ILT3 extracellular domain into an expression vector) or from naturally occurring cells. In an embodiment, the purification processes are such that no protein bands corresponding to proteins other than the desired protein are detectable by SDS-polyacrylamide gel electrophoresis (SDS-PAGE).

A variety of methods for labeling the ILT3 ligand-binding probe and the ILT3 binding probe (such as an anti-ILT3 mAb) are well known in the art, and include radioactive isotopes such as $^{125}I$, $^{32}P$, $^{35}S$, and $^{3}H$, fluorophores, chemiluminescent agents, and enzymes, and also indirect labeling with antibodies or other secondary reagent that targets and selectively binds to the ILT3 due to the high affinity of the antibody for ILT3. The choice of label depends on the sensitivity required, ease of conjugation with the primer, stability requirements, and available instrumentation. Methods for labeling polypeptides are well known in the art. See, e.g., Ausubel et A, 1992, hereby incorporated by reference.

The probes described herein can be biotinylated and detected using labeled anti-biotin antibodies or probe can be detected using avidin/streptavidin-tagged detection strategies such as enzyme reporters (e.g., horseradish peroxidase, alkaline phosphatase) in addition to the described fluorescent probes.

Antibodies

The anti-ILT3 antibody can be a polyclonal or a monoclonal antibody. The anti-ILT3 antibody is preferably a humanized antibody. In one embodiment of the methods described herein, the anti-ILT3 antibody is a fully human antibody, mono- or polyclonal. The antibodies described herein may be non-cytolytic antibodies, such as in those embodiments where anti-ILT3 is used as a secondary reagent that binds to ILT3 that is bound to ILT3 ligand on a cancer cell.

Various procedures known within the art may be used for the production of polyclonal or monoclonal antibodies directed against a polypeptide of the invention, or against derivatives, fragments, analogs homologs or orthologs thereof. See, for example, ANTIBODIES: A LABORATORY MANUAL, Harlow and Lane (1988) Cold Spring Harbor Laboratory Press, Cold Spring Harbor, N.Y. Some of these antibodies are discussed below. Methods for making fully human monoclonal antibodies are described in CURRENT PROTOCOLS IN IMMUNOLOGY, Ed. John E Coligan, Barbara E Bierer, David H Margulies, Ethan Shevach, Warren Strober. 1994-2006 John Wiley & Sons, Inc.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen-binding site capable of immunoreactions with a particular epitope of the antigen characterized by a unique binding affinity for it.

Monoclonal antibodies can be prepared using hybridoma methods, such as those described by Kohler and Milstein (1975) Nature, 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The human or humanized anti-ILT3 antibodies used in embodiments used in embodiments of the invention are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al. (1986) Nature, 321:522-525; Riechmann et al. (1988) Nature, 332:323-327; Verhoeyen et al. (1988) Science, 239:1534-1536), by substituting rodent CDRs or CDR sequences for the corresponding sequences of a human antibody. (See also U.S. Pat. No. 5,225,539.)

Where an "antibody" is referred to herein with respect to the invention, it is normally understood that an antigen-binding portion thereof may also be used. An antigen-binding portion competes with the intact antibody for specific binding to the antigen, which is ILT3, ILT3Fc or the ED. See generally, Fundamental Immunology, Ch. 7 (Paul, W., ed., 2nd ed. Raven Press, N.Y. (1989)) (incorporated by reference in its entirety for all purposes). Antigen-binding portions may also be produced by recombinant DNA techniques or by enzymatic or chemical cleavage of intact antibodies. In some embodiments, antigen-binding portions include Fab, Fab', F(ab')$_2$, Fd, Fv, dAb, and complementarity determining region (CDR) fragments, single-chain antibodies (scFv), chimeric antibodies, diabodies and polypeptides that contain at least a portion of an antibody that is sufficient to confer specific antigen-binding to the polypeptide.

As used herein, a Fd fragment means an antibody fragment that consists of the $V_H$ and $C_{H1}$ domains; an Fv fragment consists of the $V_L$ and $V_H$ domains of a single aim of an antibody; and a dAb fragment (Ward et al., Nature 341:544-546 (1989)) consists of a $V_H$ domain. In some embodiments, the antibody is a single-chain antibody (scFv) in which a $V_L$ and $V_H$ domains are paired to form a monovalent molecules via a synthetic linker that enables them to be made as a single protein chain. (Bird et al., Science 242:423-426 (1988) and Huston et al., Proc. Natl. Acad. Sci. USA 85:5879-5883 (1988).) In some embodiments, the antibodies are diabodies, i.e., are bivalent antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen-binding sites. (See e.g., Holliger P. et al., Proc. Natl. Acad. Sci. USA 90:6444-6448 (1993), and Poljak R. J. et al., Structure 2:1121-1123 (1994).) In some embodiments, one or more CDRs from an antibody of the invention may be incorporated into a molecule either covalently or noncovalently to make it an immunoadhesin that specifically binds to c-Met. In such embodiments, the CDR(s) may be incorporated as part of a larger polypeptide chain, may be covalently linked to another polypeptide chain, or may be incorporated noncovalently.

An anti-ILT3 antibody or antigen-binding portion thereof can be derivatized or linked to another molecule (e.g., another peptide or protein). In general, the antibodies or portion thereof are derivatized such that the ILT3 binding is not affected adversely by the derivatization or labeling. Accordingly, the antibodies and antibody portions of the invention are intended to include both intact and modified forms of the human anti-ILT3 antibodies described herein. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detection agent (such as a fluorophore or radioactive label in the diagnostic embodiments described herein), a pharmaceutical agent (such as a cytotoxic agent in order to kill the targeted cell expressing ILT3 ligand), and/or a protein or peptide that can mediate association of the antibody or antibody portion with another molecule (such as a streptavidin core region or a polyhistidine tag).

The anti-ILT3 antibodies or an antigen-binding portion thereof can comprise a label which may be a radioisotope or a particle which emits radioactive radiation. This particle may be a radioactive element in a form which can be linked to the antibody or fragment thereof, preferably in the form of a complex. For example an mAb labeled with $^{111}$Indium may be used to detect the target ILT3, and can also be used to kill targeted ILT3-expressing cancer cells if the radiation emitted is strong enough to be cytotoxic. Other suitable radioactive elements like $^{35}$S or $^{131}$I can be used. In embodiments where the particle has enough radiation to kill the targeted cancer cell, an anti-ILT3 antibody so labeled can be administered in therapeutically effective amounts to treat a subject having a cancer expressing ILT3 on its surface. Killing targeted ILT3-expressing cancers or cancer cells expressing ILT3 ligand using the T-cell coreceptor CD3 (scDb EDGCD3) is described in detail in Hoffmann P, Int J Cancer. 2005 May 20; 115(1):98-104, Serial killing of tumor cells by cytotoxic T cells redirected with a CD19-/CD3-bispecific single-chain antibody construct. In some embodiments the T cell coreceptor CD3 is bound to the antibody to facilitate killing by cytotoxic T cells.

Another type of derivatized antibody is a labeled antibody that can be used to detect or visualize the antibody after it binds to the targeted antigen. Useful detection agents with which an antibody or antigen-binding portion of the invention may be derivatized include fluorescent compounds, including fluorescein, fluorescein isothiocyanate, rhodamine, 5-dimethylamine-1-napthalenesulfonyl chloride, phycoerythrin, lanthanide phosphors and the like. An antibody can also be labeled with enzymes that are useful for detection, such as horseradish peroxidase, β-galactosidase, luciferase, alkaline phosphatase, glucose oxidase and the like. When an antibody is labeled with a detectable enzyme, it is detected by adding additional reagents that the enzyme uses to produce a reaction product that can be discerned. For example, when the agent horseradish peroxidase is present, the addition of hydrogen peroxide and diaminobenzidine leads to a colored reaction product, which is detectable. An antibody can also be labeled with biotin, and detected through indirect measurement of avidin or streptavidin binding. An antibody can also be labeled with a predetermined polypeptide epitope recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

Alternatively, the antibodies or antigen-binding portion thereof may be used to make an immunotoxin, which comprises a cytotoxic agent. Immunotoxins are human-made proteins that consist of a targeting portion like an antibody or fragment of one, linked to a toxin such as a cell toxic substance selected from the group comprising toxins, for example Taxol®, cytocalasin B, gramicidin D, ethidium bromide, emetine, mitomycin, etopside, tenopside, vincristine, vinblastine, colchicin, doxorubicin, daunorubicin, dihydroxy antracin dione, mitoxantrone, mithramycin, actinomycin D, 1-dehydrotestosteron, glycocorticoids, procain, tetracaine, lidokaine, propranolol, puromycin, any bacterial toxins including but not limited to *Pseudomonas* exotoxin PE38.

Anti-ILT3 monoclonal antibodies can be targeted against malignant cells by several mechanisms: including Radioimmunotherapy (RIT) involves the use of radioactively conjugated antibodies against cellular antigens. In some cases the isotope is radionuclide iodine-131 that emits both beta and gamma radiation and decays with a half-life of 8 days. Lymphomas are closely related to lymphoid leukemias like T-ALL and AML, which also originate in lymphocytes but typically involve only circulating blood and the bone marrow and do not usually form static tumors. Lymphomas are highly radio-sensitive malignancies, and it is expected that leukemias will also be radio-sensitive. To limit radiation exposure, in an embodiment murine antibodies or humanized murine antibodies may be useful for treatment with immunotoxins, as their higher immunogenicity promotes rapid clearance from the body compared to fully human antibodies.

Antibody-directed enzyme prodrug therapy (ADEPT) involves the application of cancer associated monoclonal antibodies which are linked to a drug-activating enzyme. Subsequent systemic administration of a non-toxic agent results in its conversion to a toxic drug, and resulting in a cytotoxic effect which can be targeted at malignant cells. Francis R J, Sharma S K, Springer C, et al. (2002). "A phase I trial of antibody directed enzyme prodrug therapy (ADEPT) in patients with advanced colorectal carcinoma or other CEA producing tumors". Br J Cancer 87 (6): 600-7.

Immunoliposomes are antibody-conjugated liposomes. Liposomes can carry drugs or therapeutic nucleotides and when conjugated with monoclonal (or polyclonal) antibodies, may be directed against malignant cells. Although this technique is still in its infancy, significant advances have been made. Immunoliposomes are particularly useful against blood cancers because of easy contact with the targeted cancer cells.

The antibodies and antigen-binding portions of the present invention can be incorporated into pharmaceutical compositions suitable for administration to a subject. Typically, the pharmaceutical composition comprises an antibody or antigen-binding portion of the invention and a pharmaceutically acceptable carrier. As used herein, "pharmaceutically acceptable carrier" means any and all solvents, dispersion media, coatings, antibacterial and antifungal agents, isotonic and absorption delaying agents, and the like that are physiologically compatible. Some examples of pharmaceutically acceptable carriers are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

The new anti-ILT3 monoclonal antibodies A, B, C, and D or a portion thereof comprising the ILT3 ligand-binding site may be used for the preparation of a medicament for the treatment of cancer that expresses ILT3 ligand such as T-ALL. An anti-ILT3 antibody can also be derivatized with a chemical group such as polyethylene glycol (PEG), a methyl or ethyl group, or a carbohydrate group. These groups are useful to improve the biological characteristics of the antibody, e.g., to increase serum half-life.

IV. EXAMPLES

Example 1

Flow Cytometry Method for Assaying the Expression of ILT3L Using Unlabeled ILT3Fc and a Labeled Secondary Reagent with Specific Affinity for ILT3Fc.

Bone marrow aspirate including peripheral blood mononuclear cells from patients with T-ALL or cultured T-ALL cell lines were incubated with 10 µg of unlabeled ILT3Fc for 30 minutes at 4° C. in 100 µl of staining buffer. The staining buffer consisted of Tris buffered saline (TBS), 1-3 mM $Mn^{2+}$, and 1% BSA or a similar formulation. Of note, ILT3Fc is preferably dissolved in a buffer compatible with the staining buffer used. Cells were washed three times in staining buffer. An appropriate negative control consisted of the same type of cells incubated with buffer alone (no ILT3Fc) or 10 µg human IgG during the first step.

The cells were then incubated with a secondary reagent (such as anti-Human ILT3 antibody) that binds to the ILT3 in the probe, wherein the secondary reagent is conjugated to a fluorophore such as PC5) for (30 minutes, 4° C.) and then washed three more times in staining buffer. Any antibody (or biologically active fragment or variant thereof) that selectively binds to ILT3 can be used as a secondary reagent. Commercially available monoclonal anti-human ILT3 monoclonal antibodies were used. Monoclonal anti-human ILT3 antibodies (designated A, B, C and D) that were made in the lab by immunizing mice with ILT3Fc were also tested (details for making anti-human ILT3 mAb are set forth in Example 3). Commercially available anti-ILT3 antibodies from R&D Systems include:

| | | | |
|---|---|---|---|
| Human ILT3/CD85k Affinity Purified Polyclonal Ab, Goat IgG | FC | AF2425 | 100 µg |
| Human ILT3/CD85k Allophycocyanin MAb (Clone 293623), Mouse IgG2A | FC | FAB24251A | 100 Tests |
| Human ILT3/CD85k Biotinylated Affinity Purified PAb, Goat IgG | FC | BAF2425 | 50 µg |
| Human ILT3/CD85k Fluorescein MAb (Clone 293623), Mouse IgG2A | FC | FAB24251F | 100 Tests |
| Human ILT3/CD85k MAb (Clone 293622), Mouse IgG2A | | MAB2425 | 100 µg |
| Human ILT3/CD85k MAb (Clone 293623), Mouse IgG2A | FC | MAB24251 | 100 µg |
| Human ILT3/CD85k Phycoerythrin MAb (Clone 293623), Mouse IgG2A | FC | FAR24251P | |

*FC in the table above means flow cytometry tested.

Also available is the antibody from Beckman Coulter IOTest® CD85k (ILT3)-PC5 PN IM3579; Item No: A46529.

A flow cytometry instrument and the appropriate acquisition/analysis software, such as BD Biosciences' FACSCalibur and Cell quest software, were used to analyze the ILT3Fc binding shown in FIGS. 1-4. T-ALL cell lines were expanded and maintained in culture. (FIG. 2(A)-(B)). Gating identifies leukemic cells in bone marrow aspirate from a patient with T-ALL are shown in FIG. 1(A)-(B). On the other hand, normal T cells from healthy individuals expressed low or no ILT3L (FIGS. 3(A)-(B)-4(A)-(B)). CD4-gated T helper cells form a healthy blood donor expressed 1% ILT3Fc binding (FIG. 3(A)-(B)). CD3-gated T cells from a healthy blood donor also expressed low ILT3Fc binding at 12%. (FIG. 4(A)-(B)).

The data generated by flow-cytometers can be plotted in a single dimension, to produce a histogram, or in two-dimensional dot plots or even in three dimensions. The regions on these plots can be sequentially separated, based on fluorescence intensity, by creating a series of subset extractions, termed "gates" or "gating."

The number of labeled cells, and optionally also the amount of label per cell, can be determined in different ways that depend on the reporter molecule. A preferred embodiment is using a fluorescent label and flow cytometry that can determine both the number of T-cells in a sample and amount of label per T-cell. Flow cytometry allows for the counting and examining of cells by suspending them in a stream of fluid and passing them by an electronic detection apparatus. This technique allows for the simultaneous analysis of the physical and/or chemical characteristics of up to thousands of particles per second in real time. Data accumulated using the flow cytometer can be analyzed using commercially available software.

Example 2

Targeted Lysis of T-ALL Cells that Express ILT3L with ILT3 Ligand-Binding Probes T-ALL cells were suspended in RPMI 1640 medium at a concentration of $2 \times 10^6$ cells/ml. First, cells were labeled with carbofluorescin diacetate (CFDA, 5 µM) for 10 minutes at 25° C., followed by thorough washing. The cells were then incubated with ILT3Fc (an ILT3 ligand-binding probe) (various concentrations, 0-250 µg/ml) for one hour at room temperature, then washed three times and incubated with rabbit complement for an additional hour.

Negative controls: the incubations were conducted without ILT3Fc, complement or both. Positive controls consisted of cells incubated with pooled human serum from allosensitized patients (containing anti HLA cytotoxic antibodies) as a first step and rabbit complement as a second step.

Finally, a viability dye (Ethidium Bromide, EtBr) was added and the cells were analyzed under a 488 nm light source. (Under 488 nm light, live cells appear green [CFDA+EtBr−] and dead cells appear red/orange [CFDA+EtBr+].)

% viability=(live cells/total cells)*100% cytotoxicity=(dead cells/total cells)*100

The method can be varied using other molecules that selectively bind to the targeted ILT3 ligand, incubating the cells with ILT3 ligand-binding probes that are not labeled, and then using a secondary reagent such as a labeled anti-ILT3 monoclonal antibody to detect the probe. The cytolytic agent may be an entity other than rabbit complement, i.e. complement from a different species, dyphteria toxin (DT), etc. Anti-human globulin (AHG) can be added to the reaction to enhance complement cytotoxicity. The readout can be accomplished by various instruments such as a flow cytometer or a microscope (equipped with the appropriate lasers/light sources to detect the live/dead labels employed.)

In the experimental conditions described above, two T-ALL cell lines were lysed (over 96-100% cytotoxicity) at all concentrations of ILT3Fc used (10-250 ug/ml). *Note that the binding of ILT3Fc itself did not lyse the cells; rather the binding of complement to the ligand was responsible for lysis.

Example 3

Methods for making Anti-Human ILT3Fc Monoclonal Antibodies (mAb)

The procedures for production of monoclonal antibody were adapted from Current Protocols in Immunology (1995) 2.5 contributed by Wayne M. Yokoyama. A person of skill in the art would know how to make mAb from the antigen.

Immunization to Produce Monoclonal Antibodies.

1. Mix equal volume of human ILT3Fc protein (1 mg/ml in PBS) and CFA (Complete Freunds adjuvant, Sigma) or IFA (Incomplete Freund's adjuvant, Sigma) in a 3-way stopcock until the two parts are completely emulsified. The emulsion with CFA is used for the first time immunization. IFA emulsion is used for the rest of the immunization and boosting.

2. Inject 0.2 ml of emulsion (100 µg of ILT3Fc protein) intraperitoneally into female BALB/cj mice of 6-7 week old (JAX MICE) on day 1, 8, 15. The immunized mice are rested for 21 days, and are then boosted with 0.2 ml emulsion with IFA. Three days after boosting, mice are sacrificed, and their spleens are taken for fusion.

Cell Fusion

1. One week before fusion, one vial of SP2/0-Ag14 myeloma cell line (drug-marked, nonsecretory; ATCC #CRL 1581) was cultured in complete DMEM medium (DMEM with 4500 mg glucose/L, 2 mM L-glutamine, 50 µg/ml gentamicin and 10% FBS, Sigma) at a cell density of no more than $10^6$/ml. One day before fusion, split the cells.

2. Spleens from the immunized mice were made into single-cell suspensions by squeezing with angled forceps. Debris was removed by passage through a fine-mesh metal screen. Transfer spleen cell suspension to a sterile 50-ml conical centrifuge tube and fill with serum-free DMEM. Centrifuge 5 min at 1500 rpm (500×g), room temperature, and discard supernatant. Lyse red blood cells (RBC) by resuspending pellet in 5 ml ammonium chloride solution. Let stand 5 min at room temperature. Add 45 ml sterile complete serum-free DMEM, and centrifuge as before. Resuspend cell pellet in serum-free medium, and wash the cells twice. Count the cells.

3. Separately harvest the SP2/0-Ag14 myeloma cells by transferring the cells to 50-ml conical centrifuge tubes. Wash myeloma cells three times with serum free DMEM medium. Count the cells.

4. Mix SP2/0-Ag14 myeloma and spleen cells from a whole spleen at a 1:10 ratio in a 50-ml conical centrifuge tube. Spin down the mixture at 500 g for 5 min and discard the supernatant. Perform the cell fusion at 37° C. by placing the tube containing the mixed-cell pellet in one of the double-beaker water baths in the laminar flow hood. Using a 1-ml pipet, add 1 ml pre-warmed 50% PEG (Sigma) to the mixed-cell pellet drop-by-drop over 1 min, stirring the cells with the pipet tip after each drop. Stir for an additional minute. Using a clean pipet, add 1 ml pre-warmed serum-free DMEM to the cell mixture drop-by-drop over 1 min, stirring after each drop. Repeat once with an additional 1 ml of pre-warmed complete serum-free DMEM. With a 10-ml pipet, add 7 ml pre-warmed serum-free DMEM drop-by-drop over 3 min. Centrifuge 5 min at 500×g, room temperature, and discard the supernatant. With a clean 10-ml pipet, forcefully discharge 10 ml prewarmed complete DMEM to the cell pellet. Repeat the step with 10 ml prewarmed complete DMEM medium until total volume of 30 ml is reached. If necessary, allow clumps to settle and disrupt with the pipet tip. Gently aspirate 10 ml of cell suspension with a 10-ml pipet. Add 2 drops (100 to 125 µl) of suspension to each well of a 96-well flat-bottom plate (Fisher Scientific); continue until entire suspension is plated. Incubate overnight in a humidified 37° C., 5% CO2 incubator.

4. After one day of incubation (day 2), add 2 drops of 1× HAT (Sigma) in complete DMEM-medium to each well with a 10-ml pipet. Replace half volume of medium in each well with 1× HAT medium on day 3, 4, 5, 6, 8, and 10. On day 15, replace the medium with 1× HT (Sigma) medium. After replacing medium with HT medium twice, feed the cells with complete DMEM medium.

Screening Primary Hybridoma Supernatants

1. Check cell growth under microscope. Screening should be performed when the growing cells occupy 10-25% space of a well.

2. Coat the immulon microplate (Fisher Scientific) with ILT3Fc and control human Ig (Sigma). Block the plates with PBS containing 0.05% Tween 20 and 0.25% BSA after coating.

3. Add the supernatant from the selected wells to ILT3Fc and Ig coated wells. Incubate the plate for 1 hour, wash 3 times. Add goat anti-mouse peroxidase antibody (Sigma). Incubate for 1 hour, and then wash 3 times. Adding the substrate prepared from peroxidase substrate tablets (Sigma). Pick up the wells which are positive for ILT3Fc but negative for human Ig. All the procedures of ELISA are performed according to manufacturer's instructions.

Subcloning the Hybridoma Cells which Produce ILT3Fc Positive but Human Ig Negative Antibody.

1. Take a spleen from normal BALB/c female mouse; prepare single spleen cells as described in cell fusion.
2. Add 50 μl of complete DMEM medium containing $10^5$ spleen cells to each well of a 96-well flat-bottom plate.
3. Take the cells from the wells which have the hybridoma cells producing anti-ILT3Fc antibodies. Add 50 μl of complete DMEM medium containing average 0.5 or 1 cell/well to each well of a 96-well flat-bottom plate containing spleen cells.
4. Check the plates for cell growth. Add or exchange medium as necessary. Once the hybridoma cells reach 10-25% space of a well, screen the supernatant from that well as described.
5. Expand and freeze the cells from the clones producing ILT3Fc specific antibody.
6. To further confirm that those monoclonal antibodies are against ILT3 molecule, use the supernatants from those clones to stain KG1.ILT3 cells by indirect immunostaining and analyzed by flow.

Materials and Methods

Patient Case Selection

A total of 61 consecutive specimens, which included 52 bone marrow and 9 peripheral blood samples, were analyzed between Jan. 1, 2003 and Dec. 31, 2006, according to a protocol approved by the IRB of Columbia University. Samples were obtained for diagnostic purposes from a total of 56 patients followed at our institution. ILT3 expression was tested on left-over samples after the diagnostic work-up has been completed. Diagnosis was established based on morphology, immunohistochemistry, flow cytometry, and cytogenetic analysis. Out of 61 specimens, 32 bone marrow and 9 peripheral blood samples were obtained from patients with AML (N=37). For the purpose of this study, leukemia cases were categorized according to the FAB criteria (Bennett et al., 1985). Cases of FAB M4, M4Eo, M5a and M5b were considered as displaying monocytic differentiation, while FAB MO, M1, M2, M3 (acute promyelocytic leukemia), M6 and M7 were not. The remaining 20 samples were obtained from patients with no evidence of bone marrow involvement, as established by clinical evaluation and morphology, flow cytometry and cytogenetic analysis. Thirteen of the non-involved samples were obtained from patients previously treated for AML (3 AML without differentiation, 5 APL, 3 AML with monocytic differentiation, 2 undefined AML types), while the remaining 7 samples were obtained from patients with other diseases (I aplastic anemia, 2 gastric B-cell lymphoma, 2 acute lymphocytic leukemia in remission, and 2 viral infections).

Clinical Parameters

The following clinical parameters were analyzed in relation to ILT3 expression by leukemic cells in patients with AML: age, gender, AML type, WBC, peripheral blood monocyte count. hemoglobin level, platelet count, frequency of blasts in peripheral blood and bone marrow, chromosomal abnormalities and overall survival.

Flow Cytometry

Immunophenotypic characterization of bone marrow and peripheral blood samples was performed using three-color flow cytometry, as previously described (57). The following monoclonal antibodies were used: anti-CD45, -CD4, -CO11e, -CD13, -CD14, -CD16, -CD33, CD34, -CD45, -CD56, -CD64, -CD117, -HLA-DR-MPO (BD BioScience, San Jose, Calif.), and ILT3 (Beckman Coulter, Miami, Fla.). Leukemic cells were considered positive for any given marker if >10% of the cells expressed that marker. All samples were tested within 48 h of collection. Cells were run and analyzed on a FACSCalibur (BD Biosciences) using CellQuestPro software.

Statistical Analysis

The relationship between ILT3expression and clinical parameters was studied using multiple regression analysis, Student's t test of significance and Chi-square test (ffiM SPSS Statistics 17.0). Kaplan Meier analysis was used to assess patient survival in ILT3+ and ILT3– AMLgroups.

Results

A. ILT3 is a Highly Specific and Sensitive Marker that can Reliably Distinguish AML m4/m5 from Other Types of AML To characterize the expression of inhibitory receptor ILT3 on normal and neoplastic hematopoietic precursors, we analyzed 20 bone marrow samples obtained from patients with no evidence of neoplastic disease and 41 specimens obtained from patients with AML. Flow cytometric analysis of non-involved bone marrow indicated that a high proportion of the CD14+ monocytes, specifically 80±9%, expressed ILT3 (FIG. 5), while granulocytes were essentially negative. This profile is similar to that previously reported for peripheral blood myelomonocytic cells (47), (57). Within the CD45dim/low side scatter (SSC) gate, which includes hematopoietic precursors, 10±8% of the gated cells (0.4±0.3% of all nucleated cells) expressed ILT3. There was no significant difference between the frequency of ILT3+ cells identified in the bone marrow samples obtained from patients previously treated for AML, who are currently disease free (N=13), and the frequency of ILT3+ precursor cells from non-AML patients (N=7). ILT3 precursors co-expressed CD33 and one or more of the following markers: CD34, CD117 (c-kit), CD13, CO11c, and CD14.

Figure 5A:
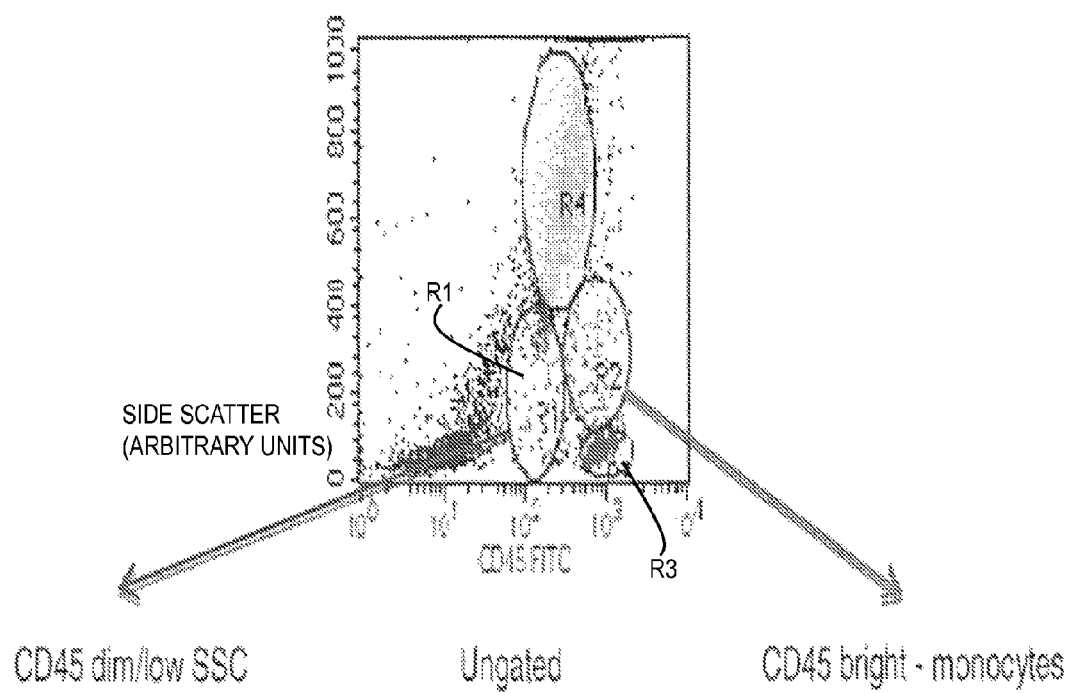
FIG. 5(A) shows all data.

Co-expression of ILT3 and B cell markers was not observed, indicating that B cell precursors do not express ILT3 (data not shown). As illustrated in FIG. 5, ILT3 positive cells included CD14+ and CD 14– cells, consistent with a maturation pattern in which ILT3 expression by bone marrow monocytic cells is acquired prior to CD14 expression. Co-expression of ILT3 and the early markers CD34 and CD 117 suggests that ILT3 is acquired at an early step of hematopoietic differentiation.

In patients with AML, leukemic cells represented 22-93% (mean±STD, 55±33%) of the bone marrow nucleated cells (N=32) or peripheral white blood cells (N=9), as determined by flow cytometry. The diagnosis of AML was confirmed by morphological, immunohistochemical and cytogenetic findings. Flow cytometric analysis indicated that ILT3 was variably expressed by the leukemic cells (range 1-99%; mean±STD, 44.±41%). However, the frequency of ILT3 positive cells in patients with AML displaying monocytic differentiation (M4/M5) was significantly higher than that observed in patients with other forms of AML, namely 65±33% versus 1±1% of the leukemic cells (p<0.0001) (Table 1). All of the 18 cases of AML m4/m5 were determined to be positive for ILT3 (ILT3+>10-15% gene), while all cases with other types of AML were negative (ILT3+~10-15%; p<0.0001; Table 1).

Figure 6:
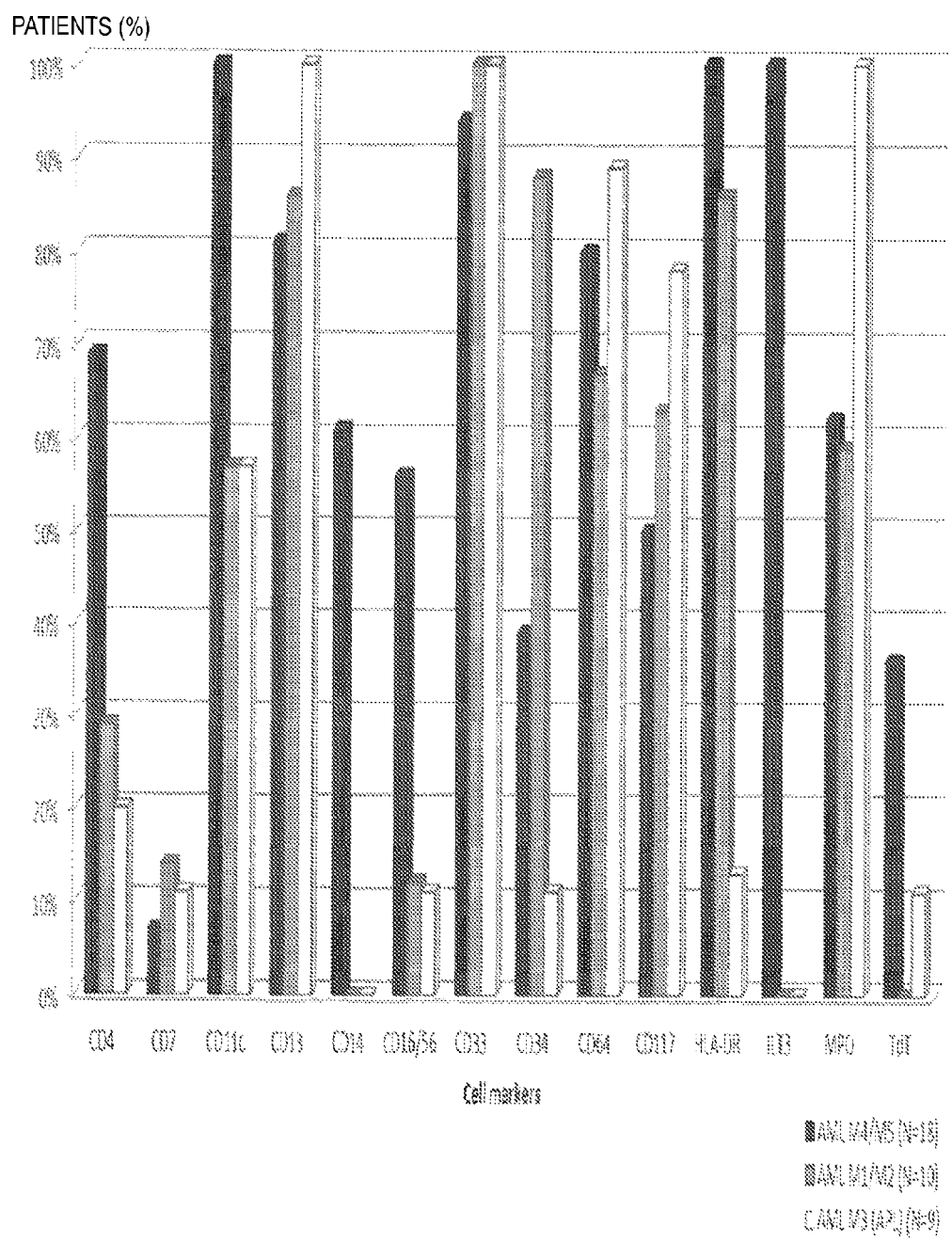
FIG. 6. is a bar graph that illustrates expression of relevant cell markers analyzed by flow cytometry in 37 patients with acute myeloid leukemia.

None of the other cellular markers was as sensitive or specific as ILT3 in distinguishing AML m4/m5 from other forms of AML (FIG. 6). Although CD11c, CD33 and HLA-DR were positive in >90% of the malignant cells from patients having AML M4/M5, these markers lacked specificity as they were only expressed in a significant fraction of other AML types. CD11c and CD33 were positive in >50% and 100%, respectively, of patients with AML M1/M2 and M3, while HLA-DR was positive in >80% of patients with AML MI/M2. Of note, the monocytic marker CDI4 was expressed in only II out of 18 cases (61%) of AML displaying monocytic differentiation. These results indicate that ILT3 is a highly specific and sensitive marker that can reliably distinguish AML m4/m5 from other types of AML.

Figure 7B:
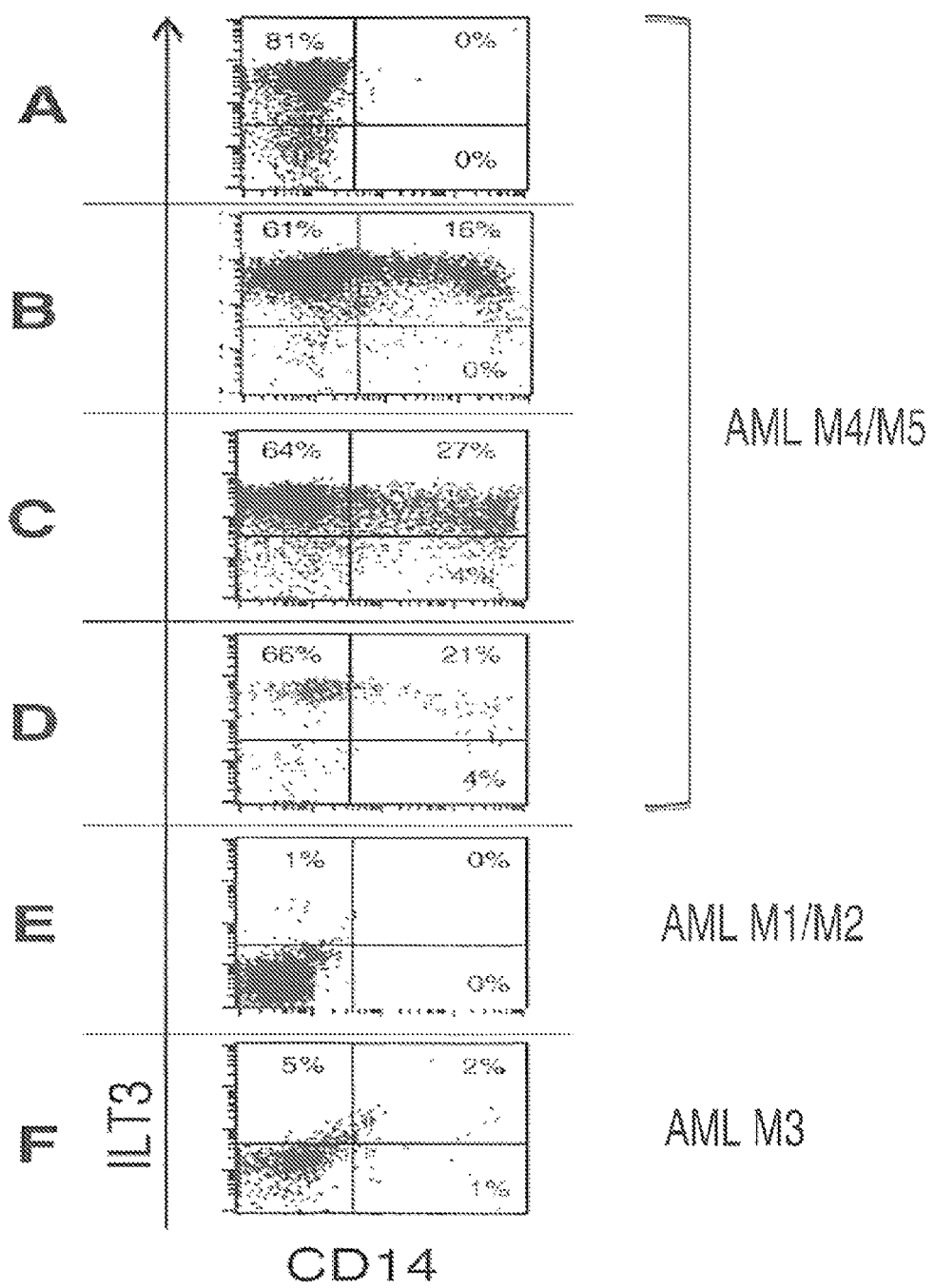
FIG. 7(B) are graphs that show results for CD14 vs ILT3 in the various panels.
Figure 7C:
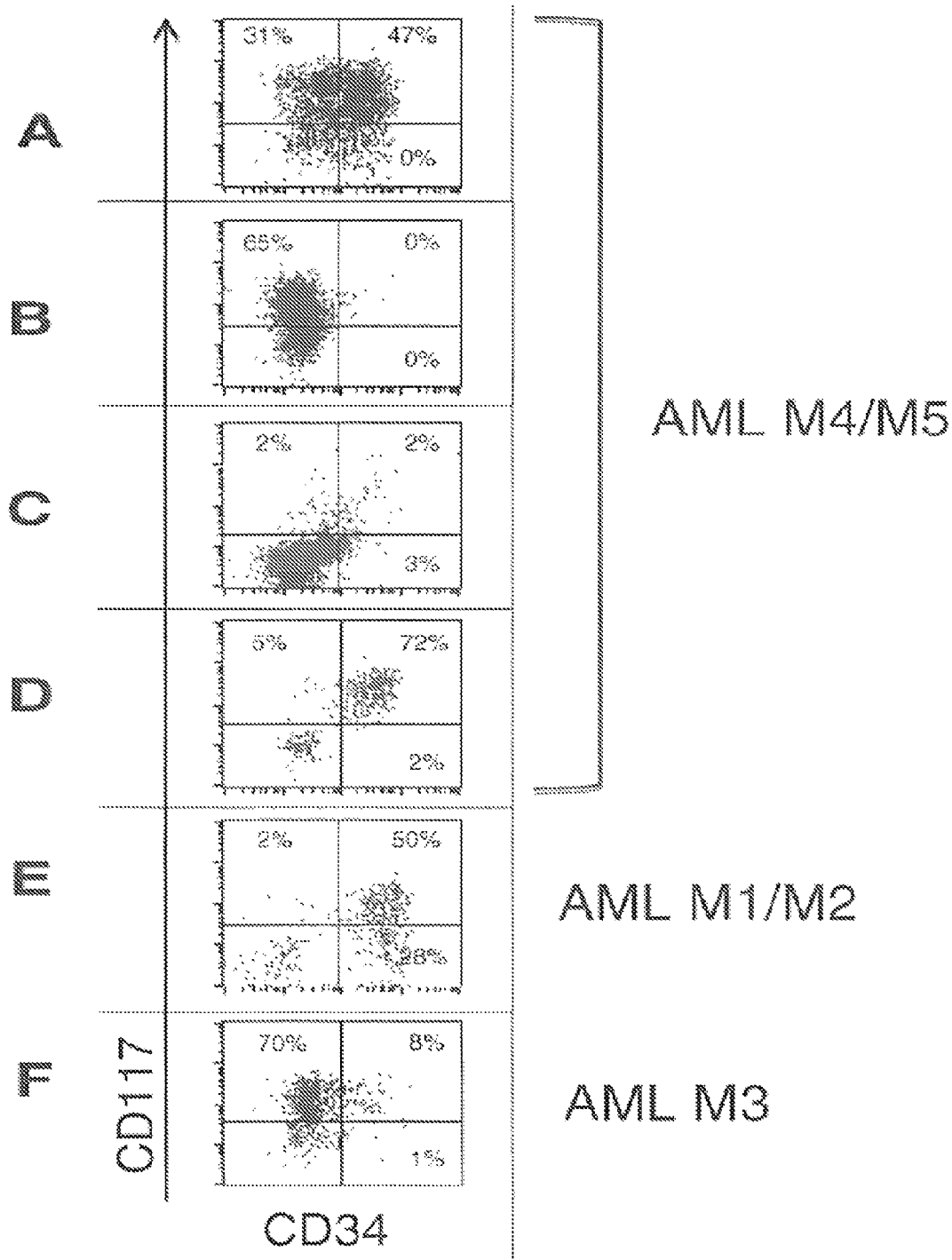
FIG. 7(C) are graphs that show results for CD34 vs CD117 in the various panels.

Notably, in patients with AML displaying monocytic differentiation, ILT3 was expressed by leukemic cells at various stages of maturation. As illustrated in FIG. 7 (panels A, B, C), ILT3 was co-expressed by CD34+/−CD117+ CD14− monoblasts and promonocytes as well as by more differentiated CD34-CD 117-CD 14+/− leukemic cells. Overall, co-expression of ILT3 and CD 117 was observed in 50%, while co-expression of ILT3 and CD34 was seen in 39% of cases with AML displaying monocytic differentiation. (FIG. 6). As described above, ILT3 was absent on leukemic cells from patients with AML lacking features of monocytic differentiation (FIG. 7E, F).

B. Use of ILT3 as a Marker for Post-Treatment Monitoring of Patients with AML

To determine whether ILT3 can be used for post-treatment monitoring of patients with AML displaying monocytic differentiation, we analyzed ILT3 expression in bone marrow samples taken from patients who relapsed after treatment. FIG. 7(D) illustrates the flow cytometric results obtained after allogeneic stem cell transplantation in a patient treated for AML with monocytic differentiation. ILT3 staining highlighted a population of monocytic precursors, which accounted for 64% of the CD45dim/low SSC cells (4% of all nucleated cells}. The frequency of ILT3+ cells within the precursor gate was significantly higher than that observed in non-involved bone marrow (FIG. 5), suggesting that the ILT3+ cells were neoplastic. These cells co-expressed CD4, CD11c, CD33, CD34, CD64, CD117, and HLA-DR and were negative for CD 14, a phenotype consistent with that of the original leukemia. Leukemia relapse was confirmed by cytogenetic analysis. These results indicate that ILT3 expression is maintained after AML treatment and is a useful marker for disease monitoring in AML with mono differentiation.

C. Statistical Significance and Clinical Correlations

As indicated above, there was a statistically significant correlation between ILT3 expression and the AML type ILT3 was positive in all AML M4/M5 cases yet in none of the M1/M2 and M3 cases (p<0.0001; Table I). Although the frequency of leukemic blasts present in the bone marrow did not vary significantly in the ILT3+ versus ILT3− AML groups, the frequency of circulating leukemic blasts was significantly lower in the ILT3+ group compared to the ILT3− group (p<0.009; Table I). Monocytosis (an increase in the number of monocytes circulating in the blood) occurred more frequently in patients with ILT3+ AML compared to patients with ILT3-AML, although the difference did not reach statistical significance (p=0.08). There were no significant differences between the two groups for the following parameters: age, gender, WBC, hemoglobin levels and platelet count.

Cytogenetic data were available for 32 patients with AML. Of these, 27 carried chromosomal abnormalities. The following cytogenetic abnormalities associated with unfavorable outcome in patients with AML were detected in our study patients: 5q deletion, monosomies of chromosomes 5 and/or 7, and complex karyotype (>3 unrelated abnormalities).

One or more of these abnormalities were detected in 5 out of 17 patients with ILT3− AML, but it was not detected in any of the patients with ILT3+ AML (p=0.046; Table 1). All patients with adverse abnormalities were from the M0-M2 subgroup. Most of the cytogenetic abnormalities associated with a favorable prognosis were found in the AML M3 (APL) group. Thus, 7 out of 10 patients from this group carried the t(15; 17) abnormality. Inv16, which has been also associated with favorable prognosis, was detected in only one patient from the ILT3+ M4/M5 group. The most frequent abnormalities found in the ILT3+ AML group were those associated with an intermediate prognosis (Table 1; p<0.001). Cytogenetic abnormalities previously associated with monocytic differentiation, namely t(9, 11) and 16q22, were observed in only 3 of 14 patients with AML m4/m5. Using multiple regression analysis, the AML type and the presence of cytogenetic abnormalities associated with intermediate prognosis were the clinical parameters most significantly correlated with ILT3 expression in our patients.

Figure 8:
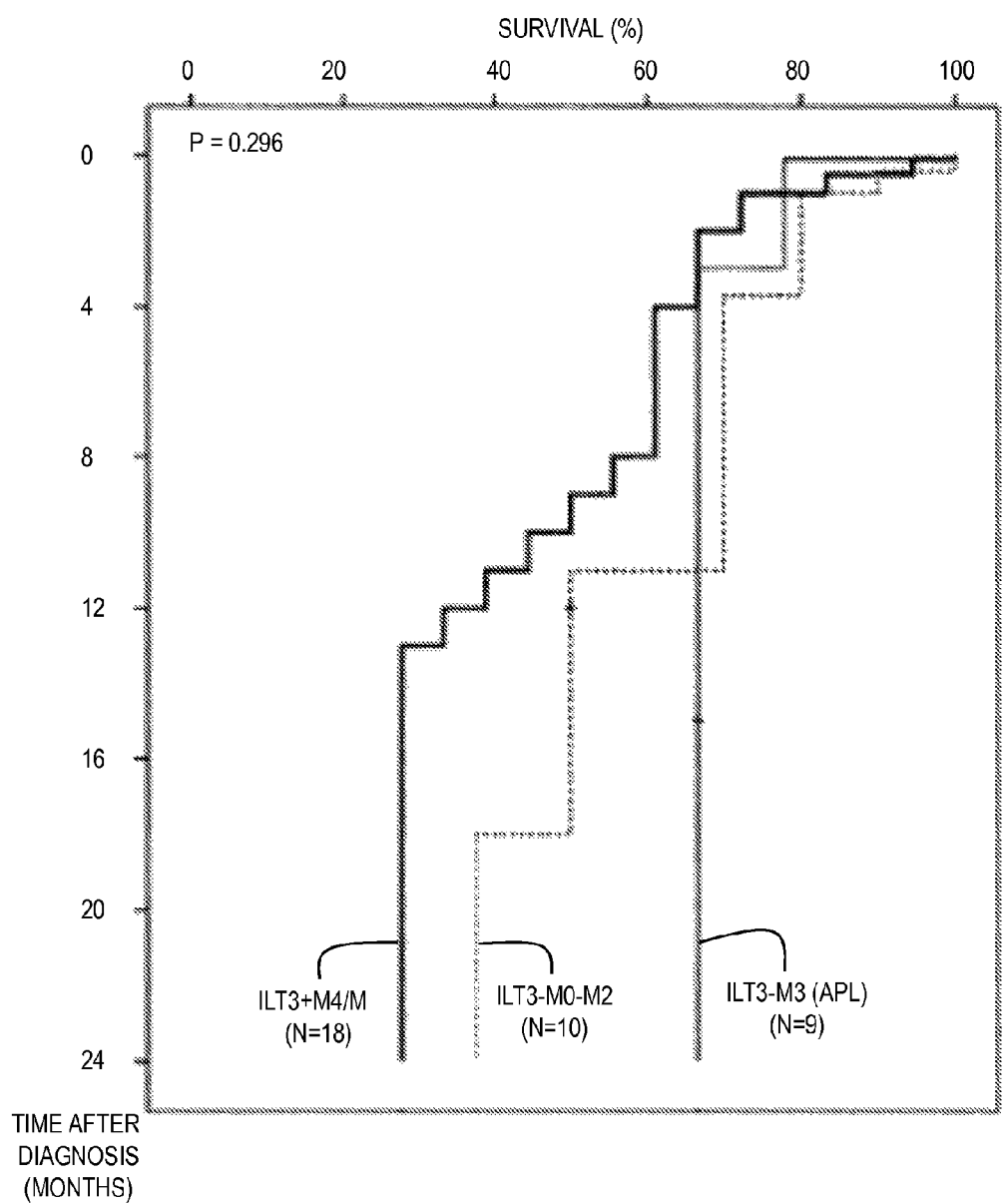
FIG. 8. is a graph that illustrates Kaplan-Meier curves illustrating patient survival within ILT3+ and ILT3− AML groups.

Patient survival in relation to ILT3 express ion was analyzed using the Kaplan-Meier analysis. As indicated in FIG. 8, patients from the ILT3 negative/M3 subgroup had the best survival, while those from the ILT3 positive/M4/M5 group tended to have the lowest survival.

Although the difference between groups did not reach statistical significance, ILT3 expression appears to have an adverse effect on survival.

In the present specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. The contents of all references, pending patent applications and published patents, cited throughout this application are hereby expressly incorporated by reference as if set forth herein in their entirety, except where terminology is not consistent with the definitions herein. Although specific terms are employed, they are used as in the art unless otherwise indicated.

REFERENCES

The entire contents of the following references are hereby incorporated by reference as if fully set forth herein, except for terminology that is inconsistent with the terminology used herein.

1. Chang C C, Liu Z, Vlad G, Qin H, Qiao X, Mancini D M, Marboe C C, Cortesini R, Suciu-Foca N. Ig like transcript 3 regulates expression of proinflammatory cytokines and migration of activated T cells. J Immunol. 1; 182(9):5208-16, 2009.
2. Vlad G, D'Agati V D, Zhang Q Y, Liu Z, Ho E K, Mohanakumar T, Hardy M A, Cortesini R, Suciu-Foca N. ILT3-Fc suppresses T cell responses to allogeneic human islet transplants in Hu-NOD/SCID mice. Diabetes 57(7): 1878-86, 2008.
3. Suciu-Foca N, Feirt N, Zhang Q Y, Vlad G, Liu Z, Lin H, Chang C C, Ho E K, Colovai A I, Kaufman H, D'Agati V D, Thaker H M, Remotti H, Galluzzo S. Cinti P, Rabitti, C, Allendorf A, Chabot J, Caricato M, Coppola R, Berloco P, Cortesini R. Soluble Ig-Like Transcript 3 Inhibits Tumor Allograft Rejection in Hu-SCID Mice and T Cell Responses in Cancer Patients. J Immunol. 178(11):7432-41, 2007.
4. Kim-Schulze, Scotto L, Vlad G, Piazza F, Lin H, Liu Z, Cortesini R, Suciu-Foca N. Recombinant Ig-Like Transcript 3-Fc Modulates T Cell Responses via Induction of Th Anergy and Differentiation of CD8+ T Suppressor Cells. J Immunol. 176(5):2790-8, 2006.
5. Kim-Schulze S, Seki T, Vlad G, Scotto L, Fan J, Colombo P C, Liu J, Cortesini R, Suciu-Foca N. Regulation of ILT3 Gene Expression by Processing of Precursor Transcripts in Human Endothelial Cells. Am J Transpl, 6(1):76-82, 2005.
6. Vlad G, Cortesini R, Suciu-Foca N. License to Heal: Bidirectional Interaction of Antigen-Specific Regulatory T Cells and Tolerogenic APC. J Immunol. 174(10): 5907-14, 2005.
7. Manavalan J S, Kim-Schulze S, Scotto L, Naiyer A J, Vlad G, Colombo P C, Marboe C, Mancini D, Cortesini R, Suciu-Foca N. Alloantigen specific CD8+CD28– FOXP3+ T suppressor cells induce ILT3+ ILT4+ tolerogenic endothelial cells inhibiting alloreactivity. Int Immunol. 16(8):1055-1068, 2004.
8. Chang C C, Ciubotariu R, Cortesini R, Colonna M, Lederman S, Dalla-Favera R, Suciu-Foca N. Tolerization of dendritic cells by T(s) cells: the crucial role of inhibitory receptors ILT3 and ILT4. Nat Immunol. 3(3):237-243, 2002.
9. Ciubotariu R, Colovai A I, Pennesi G, Liu Z, Smith D, Berlocco P. Cortesini R, Suciu-Foca N. Specific suppression of human CD4+ Th cell responses to pig MHC antigens by CD8+CD28-regulatory T cells. J. Immunol. 161:5193-5202, 1998.
10. Ciubotariu R, Liu Z, Colovai A I, Ho E, Itescu S, Ravalli S, Hardy M A, Cortesini R, Rose E A, Suciu-Foca N. Persistent allopeptide reactivity and epitope spreading in chronic rejection of organ allografts. J. Clin. Invest. 101:398-405, 1998.
11. Liu Z, Colovai A I, Tugulea S, Reed E F, Fisher P E, Mancini D, Rose E A, Cortesini, R, Michler R E and Suciu-Foca N. Indirect recognition of donor HLA-DR peptides in organ allograft rejection. J. Clin. Invest. 98:1150-1157, 1996.
12. Harris P E, Maffei A, Colovai A I, Kinne J, Tugulea S, Suciu-Foca N. Predominant HLA-class II bound self peptides of a hematopoietic progenitor cell line. Blood 87:5104-5112, 1996.
13. Liu Z, Sun Y K, Xi Y P, Maffei A, Reed E, Harris P, Suciu-Foca N. Contribution of direct and indirect recognition pathway to T cell alloreactivity. J. Exp. Med. 177:1643-1650, 1993.
14. Harris P E, Lupu F, Hong B, Reed E F, Suciu-Foca N. Differentiation stage specific "self" peptides bound by MHC-class I molecules. J. Exp. Med. 177:783-790, 1993.
15. Liu Z, Sun Y K, Xi Y P, Harris P, Suciu-Foca N. T cell recognition of self-human histocompatibility leucocyte antigens (HLA)-DR peptides in context of syngeneic HLA-DR molecules. J. Exp. Med. 175:1663-1668, 1992.
16. Harris P E, Strba-Cechova K, Rubinstein P, Mann D, King D W, Suciu-Foca N. Amplification of T cell blastogenic responses in healthy individuals and patients with acquired immunodeficiency syndrome. J. Clin. Invest. 85:746-756, 1990.
17. Reed E, Hardy M. Benvenisty A, Lattes C, Brensilver J, McCabe R, Reemstma K. King D W, Suciu-Foca N. Effect of anti-idiotypic antibodies to HLA on graft survival in renal-allograft recipients. New Engl. J. Med. 316:1450-1455, 1987.
18. Sangster R N, Minowada, J. Suciu-Foca N, Minden M, Mak T W. Rearrangement and expression of the α, β, and γ chain T cell receptor genes in human thymic leukemia cells and functional T cells. J. Exp. Med. 163:1491-1508, 1986.
19. Suciu-Foca N, Reed E, Rubinstein P, MacKenzie W, Ng A. King D W. A late differentiation antigen (LDA1) associated with the helper inducer function of human T lymphocytes. Nature 318:465-467, 1985.
20. Kronenberg M, Goverman J, Haars R, Malissen M, Kraig E. Phillips L, Delovitch T. Suciu-Foca N, Hood L. Rearrangement and transcription of the beta-chain genes of the T cell antigen receptor in different types of murine lymphocytes. Nature 313:647-653, 1985.
21. Toyonaga B, Yanagi Y, Suciu-Foca N, Mindem M, Mak T W. Rearrangements of the T cell receptor gene YT35 in human DNA from thymic leukemic T cell lines and functional helper, killer and suppressor T cell clones. Nature. 311:385-387, 1984.
22. Yoshikai Y, Yanagi Y, Suciu-Foca N, Mak T W. Presence of T cell receptor mRNA in functionally distinct T cells and elevation during intrathymic differentiation. Nature 310:506-508.1984.
23. Suciu-Foca N, Rubinstein P, Popovic M, Gallo R C, King D W. Reactivity of HTLV transformed human T cell lines to MHC Class-II antigens. Nature 321:275-277, 1984.
24. Hoffmann P, Int J Cancer. 2005 May 20; 115(1):98-104, Serial killing of tumor cells by cytotoxic T cells redirected with a CD19–/CD3-bispecific single-chain antibody construct.
25. Swerdlow S H, Campo E, Harris N L, Jaffe E S, Pileri S A, Stein H, Thiele J, Vardiman J W, editor. WHO classification of tumors of hematopoietic and lymphoid tissues, Fourth edition. Lyon: International Agency for Research and Cancer; 2008.
26. Foran J M. New prognostic markers in acute myeloid leukemia: perspective from the clinic. Hematology Am Soc Hematol Educ Program. 2010; 2010:47-55.
27. Becker M W, Jordan C T. Leukemia stem cells in 2010: current understanding and future directions. Blood Rev. 2011 March; 25(2):75-81.
28. Estey E, Dohner H. Acute myeloid leukaemia. Lancet. 2006 Nov. 25; 368(9550): 1894-907.
29. Marcucci G, Haferlach T, Dohner H. Molecular genetics of adult acute myeloid leuke rrti a: prognostic and therapeutic implications. J Clin Oncol. 2011 Feb. 10; 29(5): 475-86.
30. Schlenk R F, Dohner K, Krauter J, Frohling S, Corbacioglu A, Bullinger L, et al. Mutations and treatment outcome in cytogenetically normal acute myeloid leukemia. N Engl J Med. 2008 May 1; 358(18): 1909-18.
31. Bacher U, Kern W, Schnittger S, Hiddemann W, Schoch C, Haferl ach T. Further correlations of morphology according to FAB and WHO classification to cytogenetics in de novo acute myeloid leukemia: a study on 2,235 patients. Ann Hematol. 2005 November; 84(12):785-91.
32. Byrd J C, Mrozek K, Dodge R K, Carroll A J, Edwards C G, Arthur D C, et al. Pretreatment cytogenetic abnormalities are predictive of induction success, cumulative incidence of relapse, and overall survival in adult patients with de novo acute myeloid leukemia: results from Cancer and Leukemia Group B (CALGB 8461). Blood. 2002 Dec. 15; 100(13):4325-36.

33. Grimwade D, Hills R K, Moorman A V, Walker H, Chatters S. Goldstone A H, et al. Refinement of cytogenetic classification in acute myeloid leukemia: determination of prognostic significance of rare recurring chromosomal abnormalities among 5876 younger adult patients treated in the United Kingdom Medical Research Council trials. Blood. 2010 Jul. 22; 116(3):354-65.

34. Santamaria C M, Chillon M C, Garcia-Sanz R, Perez C, Caballero M D, Ramos F, et al. Molecular stratification model for prognosis in cytogenetically normal acute myeloid leukemia. Blood. 2009 Jul. 2; 114(1):148-52.

35. Mardis E R, Ding L, Dooling D J, Larson D E, McLellan M D, Chen K, et al. Recurring mutations found by sequencing an acute myeloid leukemia genome. N Engl J Med. 2009 Sep. 10; 361(11):1058-66.

36. Tallman M S. Relevance of pathologic classifications and diagnosis of acute myeloid leukemia to clinical trials and clinical practice. Cancer Treat Res. 2004; 121:45-67.

37. Dohner H, Estey E H, Amadori S, Appelbaum F R, Buchner T, Burnett A K, et al. Diagnosis and management of acute myeloid leukemia in adults: recommendations from an international expert panel, on behalf of the European Leukemia Net. Blood. 2010 Jan. 21; 115(3): 453-74.

38. Appelbaum F R, Gundacker H, Head D R, Slovak M L, Willman C L, Godwin J E, et al. Age and acute myeloid leukemia. Blood. 2006 May 1; 107(9):3481-5.

39. Poll yea D A, Kohrt H E, Medeiros B C. Acute myeloid leukaemia in the elderly: a review. Br J Haematol. 2011 March; 152(5):524-42.

40. Klco J M, Kulkami S, Kreisel F H, Nguyen T D, Hassan A, Frater J L. Immunohistochemical analysis of monocytic leukemias: usefulness of CD14 and Kruppel-like factor 4, a novel monocyte marker. Am J Clin Pathol. 2011 May; 135(5):720-30.

41. Manaloor E J, Neiman R S, Heilman D K, Albitar M, Casey T, Vattuone T, et al. Immunohistochemistry can be used to subtype acute myeloid leukemia in routinely processed bone marrow biopsy specimens. Comparison with flow cytometry. Am J Clin Pathol. 2000 June; 113(6):814-22.

42. Garcia C, Gardner D, Reichard K K. CD 163: a specific immunohistochemical marker for acute myeloid leukemia with monocytic differentiation. Appl Immunohistochem Mol Morphol. 2008 October; 16(5):417-21.

43. Harms P W, Bandarchi B, MaL. CD163 expression in leukemia cutis. J Cutan Pathol. 2010 September; 37(9): 953-7.

44. Dunphy C H, Tang W. The value of CD64 expression in distinguishing acute myeloid leukemia with monocytic differentiation from other subtypes of acute myeloid leukemia: a flow cytometric analysis of 64 cases. Arch Pathol Lab Med. 2007 May; 131(5):748-54.

45. Gorczyca W. Flow cytometry immunophenotypic characteristics of monocytic population in acute monocytic leukemia (AML-M5), acute myelomonocytic leukemia (AML-M4), and chronic myelomonocytic leukemia (CMML). Methods Cell Bioi. 2004; 75:665-77.

46. Dunphy C H, Orton S O, Mantell J. Relative contributions of enzyme cytochemistry and flow cytometric immunophenotyping to the evaluation of acute myeloid leukemias with a monocytic component and of flow cytometric immunophenotyping to the evaluation of absolute monocytoses. Am J Clin Pathol. 2004 December; 122(6):865-74.

47. Cella M, Dohring C, Samaridis J, Des sing M, Brockhaus M, Lanzavecchia A, et al. A novel inhibitory receptor (IL T3) expressed on monocytes, macrophages, and dendritic cells involved in antigen processing. J Exp Med. 1997 May 19; 185(10):1743-51.

48. Kim-Schulze S, Seki T, Vlad G, Scotto L, Fan J, Colombo P C, et al. Regulation of ILT3 gene expression by processing of precursor transcripts in human endothelial cells. Am J Transplant. 2006 January; 6(1):76-82.

49. Mori Y, Tsuji S, Inui M, Sakamoto Y, Endo S, Ito Y, et al. Inhibitory immunoglobulin like receptors LILRB and PIR-B negatively regulate osteoclast development. J Immunol. 2008 Oct. 1; 181(7):4742-51.

50. Ravetch J V, Lanier L L. Immune inhibitory receptors. Science. 2000 Oct. 6; 290(5489):84-9.

51. Anderson K J, Allen R L. Regulation of T-cell immunity by leucocyte immunoglobulin like receptors: innate immune receptors for self on antigen-presenting cells. Immunology. 2009 May; 127(1):8-17.

52. Lu H K, Rentero C, Raftery M J, Borges L, Bryant K, Tedla N. Leukocyte Ig-like receptor B4 (LILRB4) is a potent inhibitor of FcgammaRI-mediated monocyte activation via dephosphorylation of multiple kinases. J Bioi Chem. 2009 Dec. 11; 284(50):34839-48.

53. Chang C C. Ciubotariu R, Manavalan J S, Yuan J, Colovai A I, Piazza F, et al. Tolerization of dendritic cells by T(S) cells: the crucial role of inhibitory receptors ILT3 and ILT4. Nat Immunol. 2002 March; 3(3):237-43.

54. Chang C C, Liu Z, Vlad G, Qin H, Qiao X, Mancini D M, et al. Ig-like transcript 3 regulates expression of proinflammatory cytokines and migration of activated T cells. J Immunol. 2009 May 1; 182(9):5208-16.

55. Chang C C, Vlad G, D'Agati V D, Liu Z, Zhang Q Y, Witkowski P, et al. BCL6 is required for differentiation of lg-like transcript 3-Fc-induced CD8+ T suppressor cells. J Immunol. 2010 Nov. 15; 185(10):5714-22.

56. Munitz A. Inhibitory receptors on myeloid cells: new targets for therapy? Pharmacal Ther. 2010 January; 125 (1):128-37.

57. Colovai A I, Tsao L, Wang S, Lin H, Wang C, Seki T, et al. Expression of inhibitory receptor ILT3 on neoplastic B cells is associated with lymphoid tissue involvement in chronic lymphocytic leukemia. Cytometry B Clin Cytom. 2007 September; 72(5):354-62.

58. Marcucci G, Radmacher M D, Maharry K, Mrozek K, Ruppert A S, Paschka P, et al. MicroRNA expression in cytogenetically normal acute myeloid leukemia. N Engl J Med. 2008 May 1; 358(18):1919-28.

59. Haferlach C. Mecucci C, Schnittger S, Kohlmann A, Mancini M, Cuneo A, et al. AML with mutated NPM1 carrying a normal or aberrant karyotype show overlapping biologic, pathologic, immunophenotypic, and prognostic features. Blood. 2009 Oct. 1; 114(14):3024-32.

60. Valk P J, Verhaak R G, Beijen M A, Erpelinck C A, Barjesteh van Waalwijk van DoornKhosrovani S. Boer J M, et al. Prognostically useful gene-expression profiles in acute myeloid leukemia. N Engl J Med. 2004 Apr. 15; 350(16):1617-28.

61. Lutherborrow M, Bryant A, Jayaswal V. Agapiou D, Palma C, Yang Y H, et al. Expression profiling of cytogenetically normal acute myeloid leukemia identifies microRNAs that target genes involved in monocytic differentiation. Am J Hematol. 2011 January; 86(1):2-11.

62. Spoo A C, Lubbert M, Wierda W G, Burger J A. CXCR4 is a prognostic marker in acute myelogenous leukemia. Blood. 2007 Jan. 15; 109(2):786-91.

63. Becker P S, Kopecky K J, Wilks A N, Chien S, Harlan J M, Willman C L, et al. Very late antigen-4 function of myeloblasts correlates with improved overall survival for patients with acute myeloid leukemia. Blood. 2009 Jan. 22; 113(4):866-74.

64. Bruggemann M, Raff T, Flohr T, Gokbuget N, Nakao M, Droese J, et al. Clinical significance of minimal residual disease quantification in adult patients with standard-risk acute lymphoblastic leukemia. Blood. 2006 Feb. 1; 107 (3):1116-23.
65. Kronke J, Schlenk R F, Jensen K O, Tschurtz F, Corbacioglu A, Gaidzik V I, et al. Monitoring of minimal residual disease in NPMl-mutated acute myeloid leukemia: a study from the German-Austrian acute myeloid leukemia study group. J Clio Oncol. 2011 Jul. 1; 29(19): 2709-16.
66. San Miguel J F, Vidriales M B, Lopez-Berges C, Diaz-Mediavilla J, Gutierrez N, Canizo C, et al. Early immunophenotypical evaluation of minimal residual disease in acute myeloid leukemia identifies different patient risk groups and may contribute to postinduction treatment stratification. Blood. 2001 Sep. 15; 98(6):1746-51.
67. Sioud M. Floisand Y. TLR agonists induce the differentiation of human bone marrow CD34+ progenitors into CO11e+ CD80/86+ DC capable of inducing a Thl-type response. Eur J Immunol. 2007 October; 37(10):2834-46.
68. De Luca K, Frances-Duvert V, Asensio M J, Ihsani R, Debien E, Taillardet M, et al. The TLR1/2 agonist PAM (3)CSK(4) instructs commitment of human hematopoietic stem cells to a myeloid cell fate. Leukemia. 2009 November; 23(11):2063-74.
69. Esplin B L, Shimazu T, Weiner R S, Garrett K P, Nie L, Zhang Q, et al. Chronic exposure to a TLR ligand injures hematopoietic stem cells. J Immunol. 2011 May 1; 186 (9):5367-75.
70. Ujike A, Takeda K, Nakamura A, Ebihara S. Akiyama K, Takai T. Impaired dendritic cell maturation and increased T(H)2 responses in PIR-B(−/−) mice. Nat Immunol. 2002 June; 3(6):542-8.
71. Geissmann F, Manz M G, Jung S, Sieweke M H, Merad M, Ley K. Development of monocytes, macrophages, and dendritic cells. Science. 2010 Feb. 5; 327(5966):656-61.
72. Fogg D K, Sibon C, Miled C, Jung S, Aucouturier P, Littman D R, et al. A clonogenic bone marrow progenitor specific for macrophages and dendritic cells. Science. 2006 Jan. 6; 311 (5757):83-7.
73. Manavalan J S, Kim-Schulze S, Scotto L, Naiyer A J, Vlad G, Colombo P C, et al. Alloantigen specific CD8+ CD28−FOXP3+ T suppressor cells induce IL T3+ ILT4+ tolerogenic endothelial cells, inhibiting alloreactivity. Int Immunol. 2004 August; 16(8): 1055-68.
74. Jiang L, Barclay A N. New assay to detect low-affinity interactions and characterization of leukocyte receptors for collagen including leukocyte-associated Ig-like receptor-1 (LAIR-I). Eur J Immunol. 2009 April; 39(4):1167-75.
75. Suciu-Foca N, Feirt N. Zhang Q Y, Vlad G, Liu Z, Lin H, et al. Soluble lg-like transcript 3 inhibits tumor allograft rejection in humanized SCID mice and T cell responses in cancer patients. J Immunol. 2007 Jun. 1; 178(11):7432-41.
76. Vlad G, D'Agati V D, Zhang Q Y, Liu Z, HoEK, Mohanakumar T, et al. Immunoglobulin like transcript 3-Fc suppresses T-cell responses to allogeneic human islet transplants in huNOD/SCID mice. Diabetes. 2008 July; 57(7):1878-86.
77. Cheng H, Mohammed F, Nam G, Chen Y, Qi J, Garner L I, et al. Crystal structure of leukocyte Ig-like receptor LILRB4 (ILT3/LIR-5/CD85k): a myeloid inhibitory receptor involved in immune tolerance. J Bioi Chern. 2011 May 20; 286(20): 18013-25.
78. Cao W. Bover L, Cho M, Wen X, Hanabuchi S, Bao M, et al. Regulation of TLR7/9 responses in plasmacytoid dendritic cells by BST2 and IL T7 receptor interaction. J Exp Med. 2009 Jul. 6; 206(7):1603-14

What is claimed is:

1. A method of treating T-cell acute lymphoblastic leukemia comprising
   (a) identifying a subject that has T-cell acute lymphoblastic leukemia;
   (b) administering to the subject an amount of ILT3Fc, the extracellular domain of ILT3 or a fragment thereof comprising the ILT3 ligand binding site or combinations thereof, which ILT3Fc, extracellular domain and fragment is linked either to a radioactive isotope that emits radiation at a level that kills the leukemia cell or to a cytotoxic agent;
   (c) obtaining a pre-treatment and a post-treatment biological test sample from the subject;
   (d) contacting the samples with an ILT3 ligand-binding probe under conditions that permit the probe to bind to T-cell acute lymphoblastic leukemia cancer cells;
   (e) determining the number of T-cell acute lymphoblastic leukemia cells that are bound to the probe in the pre and post treatment samples; and
   (f) determining that the subject is responding to treatment if the number of T-cell acute lymphoblastic leukemia cells in the pre-treatment sample is significantly higher than the number of T-cell acute lymphoblastic leukemia cells in the posttreatment sample.

2. A method of treating an ILT3 ligand-expressing cancer comprising,
   a) identifying a subject in need of treatment for a cancer that expresses ILT3 ligand on its surface, and
   b) administering to the subject therapeutically effective amounts of ILT3Fc, the extracellular domain of ILT3 or a fragment thereof comprising the ILT3 ligand binding site or combinations thereof, which ILT3Fc, extracellular domain and fragment is linked either to a radioactive isotope that emits radiation at a level that kills the cancer cell or to a cytotoxic agent, thereby treating the subject for the ILT3 ligand-expressing cancer, wherein the cancer that expresses ILT3 ligand is T-cell acute lymphoblastic leukemia (T-ALL).

3. The method according to claim 2, wherein the cytotoxic agent is a member selected from the group consisting of Taxol, *Pseudomonas* exotoxic fragment, cytocalasin B, gramicidin D, ethidium bromide, emetine, mitomycin, etopside, tenopside, vincristine, vinblastine, colchicin, doxorubicin, daunorubicin, dihydroxy antracin dione, mitoxantrone, mithramycin, actinomycin D, 1-dehydrotestosteron, glycocorticoids, procain, tetracaine, lidokaine, propranolol, puromycin, and combinations thereof.

* * * * *